United States Patent
Eidenschink et al.

(10) Patent No.: US 8,694,076 B2
(45) Date of Patent: Apr. 8, 2014

(54) ELECTROACTIVE POLYMER RADIOPAQUE MARKER

(75) Inventors: Tracee Eidenschink, Wayzata, MN (US); Karl A. Jagger, Deephaven, MN (US); Derek Sutermeister, Eden Prairie, MN (US); Angela Kornkven Volk, Rogers, MN (US); Derek Wise, New Brighton, MN (US); Matt Heidner, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2013 days.

(21) Appl. No.: 11/481,468

(22) Filed: Jul. 6, 2006

(65) Prior Publication Data

US 2008/0021313 A1 Jan. 24, 2008

(51) Int. Cl.
*A61B 6/00* (2006.01)

(52) U.S. Cl.
USPC .......................................... 600/431; 604/459

(58) Field of Classification Search
USPC ............ 600/431, 424; 604/529; 606/116, 191
See application file for complete search history.

(56) References Cited

U.S. PATENT DOCUMENTS

| | | | |
|---|---|---|---|
| 4,866,132 A | 9/1989 | Obligin et al. | 525/107 |
| 4,882,392 A | 11/1989 | Smid et al. | 525/328.6 |
| 5,024,232 A | 6/1991 | Smid et al. | 128/654 |
| 5,122,136 A | 6/1992 | Guglielmi et al. | 606/32 |
| 5,256,334 A | 10/1993 | Smid et al. | 252/478 |
| 5,354,295 A | 10/1994 | Guglielmi et al. | 606/32 |
| 5,540,680 A | 7/1996 | Guglielmi et al. | 606/32 |
| 5,573,520 A | 11/1996 | Schwartz et al. | 604/282 |
| 5,752,935 A | 5/1998 | Robinson et al. | 604/97 |
| 5,755,770 A | 5/1998 | Ravenscroft | 623/1 |
| 5,759,175 A | 6/1998 | Ariola et al. | 604/96 |
| 5,824,046 A | 10/1998 | Smith et al. | 623/1 |
| 5,855,565 A | 1/1999 | Bar-Cohen et al. | 604/104 |
| 5,855,578 A | 1/1999 | Guglielmi et al. | 606/32 |
| 5,895,385 A | 4/1999 | Guglielmi et al. | 606/32 |
| 5,925,037 A | 7/1999 | Guglielmi et al. | 606/32 |
| 5,938,696 A * | 8/1999 | Goicoechea et al. | 606/194 |
| 5,944,714 A | 8/1999 | Guglielmi et al. | 606/32 |
| 5,947,963 A | 9/1999 | Guglielmi | 606/32 |
| 5,977,612 A | 11/1999 | Bour et al. | 257/618 |
| 6,010,498 A | 1/2000 | Guglielmi | 606/32 |

(Continued)

FOREIGN PATENT DOCUMENTS

| | | |
|---|---|---|
| EP | 0619749 B1 | 4/2000 |
| WO | 2007109756 | 9/2007 |
| WO | 2007126520 | 11/2007 |

OTHER PUBLICATIONS

Croce et al., The Role of Conductive Polymers in Advanced Electrochemical Technology, *Electrochim Acta* 255 (1994), vol. 39, No. 2, pp. 225-263.

(Continued)

*Primary Examiner* — Unsu Jung
*Assistant Examiner* — Saurel J Selkin
(74) *Attorney, Agent, or Firm* — Vidas, Arrett & Steinkraus, P.A.

(57) ABSTRACT

The invention relates to an expandable marker device having a pre-delivery state, a delivery state and at least one active region. The at least one active region incorporates electroactive polymer material. In addition, the expandable marker includes at least one radiopaque material to enhance observation through a medical imaging device.

21 Claims, 21 Drawing Sheets

(56) References Cited

U.S. PATENT DOCUMENTS

| | | | |
|---|---|---|---|
| 6,040,408 A | 3/2000 | Koole | 526/292.1 |
| 6,056,700 A | 5/2000 | Burney et al. | 600/564 |
| 6,059,812 A | 5/2000 | Clerc et al. | 606/198 |
| 6,066,133 A | 5/2000 | Guglielmi et al. | 606/32 |
| 6,077,880 A | 6/2000 | Castillo et al. | 523/105 |
| 6,083,220 A | 7/2000 | Guglielmi et al. | 606/32 |
| 6,117,296 A | 9/2000 | Thomson | 204/607 |
| 6,179,851 B1 | 1/2001 | Barbut et al. | 606/159 |
| 6,200,338 B1 | 3/2001 | Solomon et al. | 623/1.34 |
| 6,234,177 B1 * | 5/2001 | Barsch | 128/897 |
| 6,249,076 B1 | 6/2001 | Madden et al. | 310/363 |
| 6,267,775 B1 | 7/2001 | Clerc et al. | 606/198 |
| 6,315,790 B1 | 11/2001 | Gerberding et al. | 623/1.11 |
| 6,361,759 B1 | 3/2002 | Frayne et al. | 424/9.323 |
| 6,388,043 B1 | 5/2002 | Langer et al. | 528/80 |
| 6,514,193 B2 | 2/2003 | Kaplan | 600/7 |
| 6,514,237 B1 | 2/2003 | Maseda | 604/533 |
| 6,517,237 B1 | 2/2003 | Hammond et al. | 374/31 |
| 6,530,934 B1 | 3/2003 | Jacobsen et al. | 606/157 |
| 6,540,721 B1 * | 4/2003 | Voyles et al. | 604/103.1 |
| 6,641,606 B2 | 11/2003 | Ouriel et al. | 623/1.12 |
| 6,679,836 B2 | 1/2004 | Couvillon, Jr. | 600/146 |
| 6,682,537 B2 | 1/2004 | Ouriel et al. | 606/108 |
| 6,746,661 B2 | 6/2004 | Kaplan | 424/1.25 |
| 6,749,556 B2 | 6/2004 | Banik | 600/30 |
| 6,770,027 B2 | 8/2004 | Banik et al. | 600/146 |
| 6,812,624 B1 | 11/2004 | Pei et al. | 310/800 |
| 6,835,173 B2 | 12/2004 | Couvillon, Jr. | 600/146 |
| 6,888,098 B1 | 5/2005 | Merdan et al. | 219/121.72 |
| 6,921,360 B2 | 7/2005 | Banik | 600/30 |
| 6,940,211 B2 | 9/2005 | Pelrine et al. | 310/330 |
| 6,969,395 B2 | 11/2005 | Eskuri | 606/200 |
| 6,982,514 B1 | 1/2006 | Lu et al. | 310/300 |
| 6,997,870 B2 | 2/2006 | Couvillon, Jr. | 600/146 |
| 2003/0068522 A1 | 4/2003 | Wang | 428/654 |
| 2003/0120263 A1 | 6/2003 | Ouriel et al. | |
| 2003/0236445 A1 | 12/2003 | Couvillon, Jr. | 600/114 |
| 2004/0068161 A1 | 4/2004 | Couvillon, Jr. | 600/143 |
| 2004/0087982 A1 | 5/2004 | Eskuri | 606/153 |
| 2004/0143160 A1 | 7/2004 | Couvillon, Jr. | 600/114 |
| 2005/0004425 A1 | 1/2005 | Banik | 600/30 |
| 2005/0085693 A1 | 4/2005 | Belson et al. | 600/146 |
| 2005/0102017 A1 * | 5/2005 | Mattison | 623/1.11 |
| 2005/0107669 A1 | 5/2005 | Couvillon, Jr. | 600/146 |
| 2005/0165439 A1 | 7/2005 | Weber et al. | 606/191 |
| 2006/0041264 A1 | 2/2006 | Eskuri | 606/153 |
| 2006/0111618 A1 | 5/2006 | Couvillon, Jr. | 600/152 |

OTHER PUBLICATIONS

Yamaura et al., Enhancement of Electrical Conductivity of Polypyrrole Film by Stretching : Counter-ion Effect, *Synthetic Metals*, vol. 26 (1988) pp. 209-224.

Zhou et al., Actuators for the Cochlear Implant, *Synthetic Metals*, vol. 39-40 (2003) pp. 135-136.

U.S. Appl. No. 11/280,120, filed Nov. 16, 2005, Jan Weber and Tracee Eidenschink.

U.S. Appl. No. 11/411,360, filed Apr. 25, 2006, Angela Kornkven Volk et al.

U.S. Appl. No. 11/368,927, filed Mar. 6, 2006, Angela Kornkven Volk et al.

Smela et al., Thiol Modified Pyrrole Monomers : 1. Synthesis, Characterization, and Polymerization of 1-(2-Thioethyl)-Pyrrole and 3-(2-Thioethyl)-Pyrrole, *Langmuir*, vol. 14, No. 11 (1998) pp. 2970-2975 (1998).

Jager et al., Microfabricating Conjugated Polymer Actuators, *Science*, vol. 290 (2000) pp. 1540-1545.

Smela et al., Electrochemically Driven Polypyrrole Bilayers for Moving and Positioning Bulk Micromachined Silicon Plates, *J. Microelectromechanical Systems*, vol. 8, No. 4 (1999) pp. 373-383.

Madden et al,*Proceedings of the SPIE*, vol. 4329 (2001) pp. 73-83, entitled "Smart Structures and Materials 2001: Electroactive Polymer and Actuator Devices".

* cited by examiner

ELECTROACTIVE POLYMER RADIOPAQUE MARKER

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

In some embodiments this invention relates to implantable medical devices, an example of which is markers, their manufacture, and methods of use. Some embodiments are directed to delivery systems, such as catheter systems of all types, which are utilized in the delivery of such medical devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, or optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, may be radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled, or from one or more interwoven wires or braids.

The accurate positioning of a medical device or an implantable medical device such as a marker within a body lumen may be critical to the success of a medical procedure. In order to assist in the accurate placement of an implantable medical device within a lumen, fluoroscopes, X-ray machines, MRI's, and/or other viewing devices may be used to view a catheter, stent, and/or marker, as the placement of the medical device within a body lumen progresses. Frequently, a portion of the catheter, stent, and/or marker, may be formed of, coated, and/or impregnated with a radiopaque substance to enhance visualization through the viewing device.

An example of a catheter having an external metal radiopaque band may be found in U.S. Pat. No. 5,759,175 to Fischell et al which is incorporated by reference in its entirety.

It may be desirable to enhance the profile of the catheter and/or marker at certain locations within a body lumen in order to better visualize the configuration and orientation of a vessel or vessel bifurcation. The enhanced visualization of an enlarged profile marker, within a body lumen, may expedite the speed of a medical procedure, resulting in improved survivability for a patient.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All U.S. patents and applications and all other published documents mentioned anywhere in this application are incorporated herein by reference in their entirety.

Without limiting the scope of the invention, a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In at least one embodiment, an expandable marker device is provided for use in a body lumen, the medical device includes a pre-delivery configuration, a delivery configuration, and at least one active region. In at least one embodiment, an expandable marker device is provided for use on a catheter or device for insertion into a vessel. In some embodiments, the vessel is bifurcated. In some embodiments the at least one active region is at least partially formed of electroactive polymer material. In at least one embodiment, the expandable marker further incorporates a portion of radiopaque material to enhance visualization of the marker device during use of an imaging device.

In some embodiments, the electroactive polymer may be formed of either an electroactive polymer or an ionic electroactive polymer.

In at least one embodiment, the radiopaque materials may be integral to, deposited on, or embedded within the expandable marker.

In some embodiments, the radiopaque materials are formed of radiopaque polymers which are combined with electroactive polymers to form a framework, or substrate.

In at least one embodiment, the expandable marker includes a plurality of active regions which provide a transition function for the marker from a pre-delivery configuration to a delivery configuration.

In at least one embodiment, one or more expandable markers are used to map a body lumen. In some embodiments, the expandable marker frictionally engages the interior wall of a body lumen.

In some embodiments, the expandable marker will be releasably engaged to a medical device such as a catheter for placement within a body lumen during a medical procedure.

In some embodiments, the expandable marker will be engaged to a medical device such as a catheter for retraction from a body lumen upon completion of a medical procedure.

In some embodiments, the expandable marker is electrically engaged to a medical device such as a catheter, which in turn is in electrical communication with a source of anions.

In some embodiments, at least one expandable member is positioned in a vessel, proximate to a vessel bifurcation in a main vessel, in a branch vessel, proximal to the ostium of a branch vessel, or distal to the ostium of a branch vessel.

These and other embodiments which characterize the invention are pointed out with particularity in the claims annexed hereto and forming a part hereof. However, for further understanding of the invention, its advantages and objectives obtained by its use, reference should be made to the drawings which form a further part hereof and the accompanying descriptive matter, in which there is illustrated and described embodiments of the invention.

BRIEF DESCRIPTION OF THE SEVERAL VIEWS OF THE DRAWING(S)

A detailed description of the invention is hereafter described with specific reference being made to the drawings.

DETAILED DESCRIPTION OF THE INVENTION

Figure 1C:
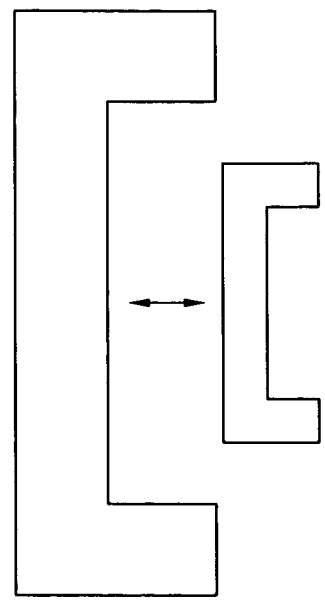
FIG. 1C shows an alternative electroactive polymer in a first state having a first volume and a second state having a different second volume.

While this invention may be embodied in many different forms, there are described in detail herein specific embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

As indicated above, at least one embodiment of the invention is directed to strategic placement or use of electroactive polymer (EAP) on, or within, a radiopaque marker device to provide the marker device with active regions. Depending on the placement of EAP, a variety of radiopaque marker characteristics may be manipulated and/or improved. For example, as shown in FIGS. 8A-10B, 17, and 19A-20B a catheter system 18 is shown equipped with an EAP radiopaque marker 10 engaged thereto. As illustrated in FIGS. 9A-9B the marker band is constructed from a substrate 52 of EAP material 50 which includes one or more regions 12 of a radiopaque material. In some embodiments the radiopaque material 12 and the EAP material 50 are combined to form a composite marker device.

In some embodiments, an expandable radiopaque marker having EAP material is utilized to improve observation through the use of any variety of imaging modalities during medical procedures. The imaging modalities include, but are not necessarily limited to the use of radiopaque observation, MRI viewing, fluoroscopy, and/or X-ray. In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

In some embodiments, the electroactive polymer material 50 may be placed on the inner and/or outer surface of the EAP radiopaque marker 10; circumferentially on the inner and/or outer surface of the EAP radiopaque marker 10; longitudinally on the inner and/or outer surface of the EAP radiopaque marker 10; internally positioned within or relative to the EAP radiopaque marker 10; woven into the EAP radiopaque marker 10; impregnated within the inner and/or outer surface of the EAP radiopaque marker 10; or on the inner and/or outer sides of the EAP radiopaque marker 10, or any combination thereof. (See generally FIGS. 3A-5B; and 7A-20B).

In at least one embodiment the EAP materials 50 may have a tensile strength greater than 160 MPa. In at least one embodiment the EAP materials 50 may have a tensile strength less than 20 MPa. In some embodiments, the EAP materials 50 selected for the EAP RO Marker 10 may have tensile strength of between 20 MPa and 160 MPa. In at least one embodiment the EAP materials 50 may have a thickness dimension of less than 1 µm. In at least one embodiment the EAP materials 50 may have a thickness dimension of greater than 100 µm. In some embodiments, the EAP materials 50 selected for the EAP RO Marker 10 may have a thickness dimension of approximately 1-100 µm.

In some embodiments, an expandable medical radiopaque marker may have EAP regions strategically incorporated into or on the radiopaque marker, in order to provide improved expansion and/or contraction control. Selective activation of the EAP regions may provide for independent selective expansion and/or contraction of one or more portions of the expandable radiopaque marker. Incremental expansion states may be provided as an intermediate size between the compact state referred to in the "B" figures and the expanded state in the "A" figures herein. For example, step-wise activation of the EAP regions may allow for incremental expansion states. Selective or incremental volumetric expansion of the EAP regions may improve the visibility of the medical radiopaque marker through an imaging modality. The selective contraction and expansion of the EAP regions preferably increases the accuracy of placement of a medical radiopaque marker or medical device within a body lumen.

In some embodiments the EAP radiopaque marker 10 includes an expandable medical radiopaque substance 12 incorporating EAP material 50 to improve observation during medical procedures. (See generally FIGS. 2A-2B; 9A-9B; 11A-11B; and 15-16). Improved viewability/detectability of the marker is obtained via the activation/deactivation of the EAP material 50.

In at least one embodiment, the EAP active regions 50 are employed for controlled expansion, such that the EAP radiopaque marker 10 is expanded incrementally to the shape or curve of a body vessel. (See generally FIGS. 19A-20B)

Figure 22A:
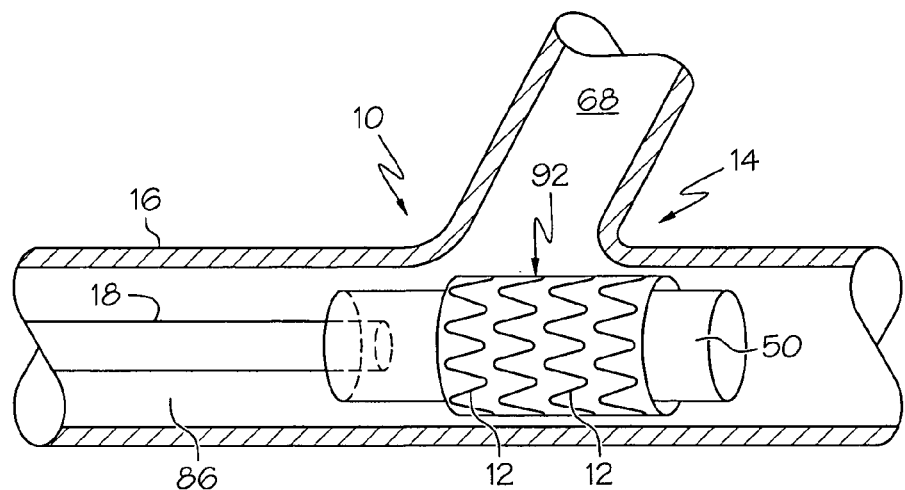
FIG. 22A shows an alternative medical device comprising an electroactive polymer and radiopaque marker in an expanded state.
Figure 22B:
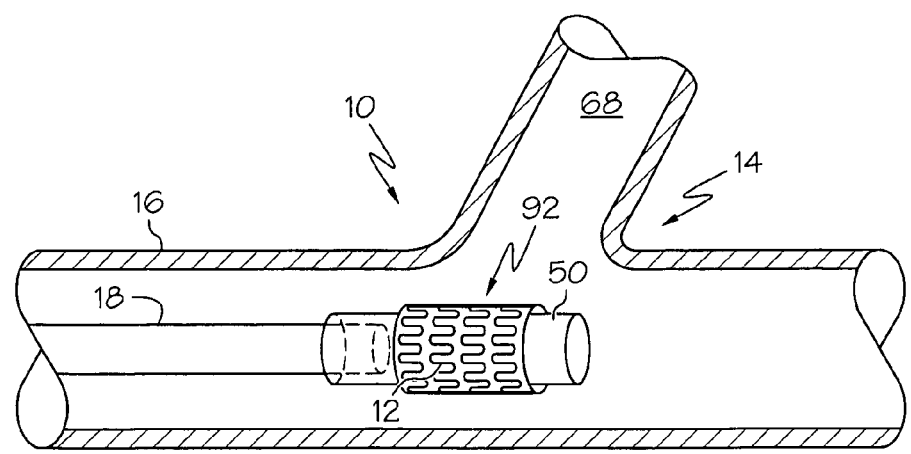
FIG. 22B shows an alternative medical device comprising an electroactive polymer and radiopaque marker in a pre-expanded state.

In some embodiments, an expandable medical radiopaque marker 92 may be disposed about a medical device formed from EAP 50. (FIGS. 22A-22B.) In one embodiment, as depicted in FIGS. 22A-22B the radiopaque elements 12 may be formed into a tubular framework for positioning to the exterior of the EAP material 50. Exposure of anions to the EAP material 50 results in the expansion of the EAP material, which in turn, causes the expansion/enlargement of the radiopaque framework 12.

In some embodiments, EAP active regions 50 may be incorporated into the outer surface of a medical device in order to decrease the coefficient of friction, and to improve surface lubricity. When activated by application of voltage, the lubricious EAP extends out from the surface of the device providing a more slippery, lubricious surface.

Electroactive polymers are characterized by their ability to change shape in response to electrical stimulation. EAPs include electric EAPs and ionic EAPs. Piezoelectric materials may also be employed but tend to undergo small deformation when voltage is applied.

Electric EAPs include ferroelectric polymers, dielectric EAPs, electrorestrictive polymers such as the electrorestrictive graft elastomers and electro-viscoelastic elastomers, and liquid crystal elastomer materials.

The radiopaque material of the rotational marker according to the invention may be actuated, at least in part, with electroactive polymer (EAP) actuators. Electroactive polymers are characterized by their ability to change shape in response to electrical stimulation. EAPs can be divided into two categories including electronic EAPs (driven by an electric field) and ionic EAPs (involving mobility or diffusion of ions).

Electronic EAPs (electrorestrictive, electrostatic, piezoelectric, ferroelectric) may be induced to change their dimensions by applied electric fields. Examples of materials in this category include ferroelectric polymers (commonly known polyvinylidene fluoride and nylon 11, for example), dielectric EAPs, electrorestrictive polymers such as the electrorestrictive graft elastomers and electro-viscoelastic elastomers, and liquid crystal elastomer composite materials wherein conductive polymers are distributed within their network structure.

In at least one embodiment, ionic EAPs may be employed in connection with the present invention. Ionic EAPs may include ionic polymer gels, ionomeric polymer-metal composites, conductive polymers and carbon nanotubes.

In some embodiments, the induced displacement of both electronic EAPs and ionic EAPs may be geometrically designed to bend, stretch or contract.

Common polymer materials such as polyethylene, polystyrene, polypropylene, etc., may be made conductive through compounding techniques involving the addition of conductive fillers which impart their conductive properties to the polymer, by forming conductive current-carrying paths through the polymer matrix. The polymer matrix may be insulative, but the composite exhibits conductive properties via the filler. These polymers are almost exclusively thermoplastic, but thermosetting materials such as epoxies, may also be employed. Suitable conductive fillers include metals and carbon (usually carbon black or fiber). These can be in the form of sputter coatings or other means may be employed through which a pattern of conductive material can be applied.

Ionic EAPs include ionic polymer gels, ionomeric polymer-metal composites, conductive polymers and combinations thereof. Upon application of a small voltage, ionic EAPs may bend significantly. Ionic EAPs also have a number of additional properties that make them attractive for use in the devices of the present invention, including the following: (a) they are lightweight, flexible, small and easily manufactured; (b) energy sources are available which are easy to control, and energy may be easily delivered to the EAP's; (c) small changes in potential (e.g., potential changes on the order of 1V) may be used to effect volume change in the EAP's; (d) they are relatively fast in actuation (e.g., full expansion/contraction in a few seconds); (e) EAP regions may be created using a variety of techniques, for example, electrodeposition; and (f) EAP regions may be patterned, for example, using one or more of the group of photolithography, ink jet, dot matrix, laser printing, and other types of printing or pattern formation, if desired.

Conductive plastics may also be employed. Conductive plastics include common polymer materials which are almost exclusively thermoplastics that require the addition of conductive fillers such as powdered metals or carbon (usually carbon black or fiber).

In some embodiments, ionic polymer gels may be activated by chemical reactions to become swollen upon a change from an acid to an alkaline environment.

Ionomeric polymer-metal composites may bend as a result of the mobility of cations in the polymer network. Suitable base polymers may include perfluorosulfonate and perfluorocarboxylate.

Essentially any electroactive polymer that exhibits contractile or expansile properties may be used in connection with the various active regions of the invention, including any of those listed above.

In some embodiments herein, the EAPs employed may be ionic EAPs. The ionic EAPs may include conductive polymers that feature a conjugated backbone (they include a backbone that has an alternating series of single and double carbon-carbon bonds, and sometimes carbon-nitrogen bonds, i.e. π-conjugation). The EAP's may have the ability to increase the electrical conductivity under oxidation or reduction reactions, in that the polymers allow for freedom of movement of electrons, therefore allowing the polymers to become conductive. The pi-conjugated polymers may be converted into electrically conducting materials by oxidation (p-doping) or reduction (n-doping).

EAP's may actuate via the reversible counter-ion insertion and expulsion that occurs during redox cycling. Dimensional or volumetric changes may be effectuated via mass transfer of ions into or out of the polymer. This ion transfer may be used to build the conductive polymer actuators. The EAP-containing active region may contract and/or expand in response to the flow of ions out of, or into, the same. For example, in some conductive polymers, expansion is believed to be due to ion insertion between chains, whereas in others inter-chain repulsion is believed to be the dominant effect. Regardless of the mechanism, the mass transfer of ions into and out of the EAP material leads to a volumetric expansion or contraction of the polymer, delivering significant stresses (e.g., on the order of 1 MPa) and/or strains (e.g., on the order of 10%). These characteristics are ideal for construction of the devices of the present invention. As used herein, the expansion or the contraction of the active region of the device is generally referred to as "actuation." These exchanges occur with small applied voltages and voltage variation may be used to control actuation speeds.

Upon application of a small voltage, as small as 1 or 2 volts, and proper design of a substrate, ionic EAPs may bend significantly. Ionic EAPs also have a number of additional properties that make them attractive for use in the devices of the present invention, including the following: (a) lightweight, flexible, small and easily manufactured; (b) energy sources are available which are easy to control, and energy can be easily delivered to the EAPS; (c) small changes in potential (e.g., potential changes on the order of 1V; d) may be used to effect volume change in the EAPs; (e) relatively fast in actuation (e.g., full expansion/contraction in a few seconds); (f) EAP regions may be created using a variety of techniques, for example, electrodeposition; and (g) EAP regions may be patterned, for example, using photolithography, if desired.

Some commonly known conductive EAPS include, but are not limited to, polypyrroles, polyanilines, polythiophenes, polyethylenedioxythiophenes, poly(p phenylenes), poly(p-phenylene vinylene)s, polysulfones, polypyridines, polyquinoxalines, polyacetylenes, polyanthraqinones, poly(n-vinylcarbazole)s, etc., with the most common being polythiophenes, polyanilines, and polypyrroles.

Some of the structures are shown below:

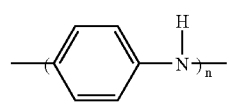

Polyaniline

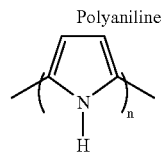

Polypyrrole

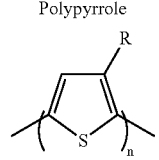

Polythiophenes

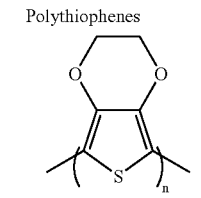

Polyethylenedioxythiophene

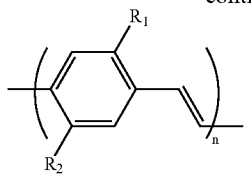

Poly(p-phenylene vinylene)s

Polypyrrole, shown in more detail below, which may be one of the most stable of these polymers under physiological conditions:

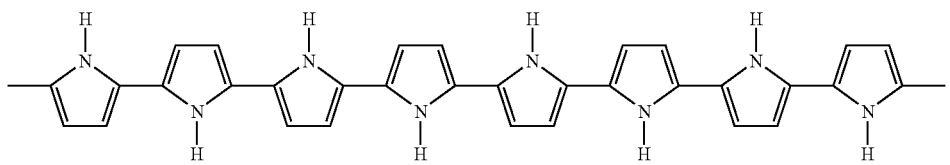

The above list is intended for illustrative purposes only, and not as a limitation on the scope of the present invention.

Additionally, the following elements are commonly utilized to bring about electroactive polymer (EAP) actuation: (a) a source of electrical potential, (b) an active region, which comprises the electroactive polymer, (c) a counter electrode and (d) an electrolyte in contact with both the active region and the counter electrode.

Ionic EAPs, driven by diffusion of ions, suitably include at least one electrolyte for the actuation mechanism. The electrolyte, which is in contact with at least one portion of the EAP, allows for the flow of ions and thus acts as a source/sink for the ions. The electrolyte may be, for example, solid, liquid or gel, providing that ion movement is permitted. Where the electrolyte is a solid, it should move with the active member of the EAP and should not be subject to delamination. Suitably, the electrolyte is preferably non-toxic in the event that a leak inadvertently occurs in vivo.

A liquid electrolyte, may be for example, an aqueous solution including at least one salt, such as a solution of NaCl, sodium dodecylbenzene sulfonate, phosphate, buffered solution, physiological solutions, or some appropriate mixture thereof. Gels include, for example, a salt doped agar gel or polymethylmethacrylate (PMMA) gel containing a salt dopant. Solid electrolytes include ionic polymers different from the EAP and salt films. Solid electrolytes include polymer electrolytes, for example, perfluorocarbon materials such as NAFION® perfluorosulfonic acid polymer available from DuPont de Nemours & Company. Solid electrolytes have also been prepared using propylene carbonate, ethylene carbonate, polyacrylonitrile and cupric perchlorate, for example. See Croce, F.; Panero, S., Passerini, S., Scrosati, B., 39 *Electrochim. Acta* 255 (1994).

The electrolyte, which is in contact with at least a portion of the surface of the EAP, allows for the flow of ions and thus acts as a source/sink for the ions. Any suitable electrolyte may be employed herein.

Counter electrode may be in electrical contact with electrolyte in order to provide a return path for charge to a source of potential difference between an EAP medical device and an electrolyte. The counter electrode may be formed using any suitable electrical conductor, for example, another conducting polymer, a conducting polymer gel, or a metal, such as stainless steel, gold, platinum, copper, etc. At least a portion of the surface of the counter electrode may be in contact with the electrolyte, in order to provide a return path for charge.

Counter electrode may be in the form of a wire, such as a wire winding, or may be applied by any suitable means including electroplating, chemical deposition, or printing. In order to activate at least a portion of an EAP device, a current is passed between the EAP material and counter electrode, inducing contraction or expansion of EAP material.

The source of electrical potential for use in connection with the present invention can be quite simple, consisting, for example, of a dc battery and an on/off switch. Alternatively, more complex systems may be utilized. For example, an electrical link may be established with a microprocessor, allowing a complex set of control signals to be sent to the EAP-containing active region(s).

Additionally, the behavior of conducting polymers such as the conjugated polymers described herein can be dramatically altered with the addition of charge transfer agents (dopants). Various dopants may be used in the EAP polypyrrole-containing active regions, including large immobile anions (P-doping) and large immobile cations (n-doping). These materials can be oxidized to a p-type doped material by doping with an anionic dopant species or reducible to a n-type doped material by doping with a cationic dopant species. Generally, polymers such as polypyrrole (PPy) are partially oxidized to produce I-doped materials:

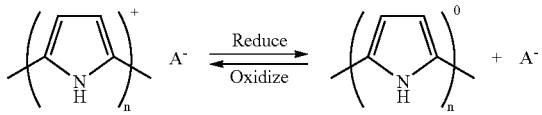

At least one embodiment, EAP polypyrrole-containing active regions may fabricated using a number of known techniques, for example, extrusion, casting, dip coating, spin coating, or electro-polymerization/deposition techniques. Such EAP active regions may also be patterned, for example, using lithographic techniques, if desired.

As a specific example, EAP polypyrrole films may be synthesized by electrodeposition according to the method described by M. Yamaura et al., "Enhancement of Electrical Conductivity of Polypyrrole Film by Stretching: Counter-ion Effect," Synthetic Metals, vol. 36, pp. 209-224 (1988), which is incorporated herein by reference.

As another specific example of a fabrication technique, EAP polypyrrole may be galvanostatically deposited on a platinised substrate from a pyrrole monomer solution using the procedures described in D. Zhou et al., "Actuators for the Cochlear Implant," *Synthetic* Metals 135-136 (2003) 39-40, the content of which is incorporated by reference herein. EAP Polypyrrole may also be deposited on gold. In some embodiments, adhesion of the electrodeposited EAP polypyrrole layer is enhanced by covering a metal such as gold with a chemisorbed layer of molecules that may be copolymerized into the polymer layer with chemical bonding. Thiol is one example of a head group for strong chemisorbtion to metal. The tail group may be chemically similar to structured groups formed in the specific EAP employed. The use of a pyrrole ring attached to a thiol group (e.g., via a short alkyl chain) is an example for a polypyrrole EAP. Specific examples of such molecules are 1-(2-thioethyl)-pyrrole and 3-(2-thioethyl)-pyrrole. See, e.g., E. Smela et al., "Thiol Modified Pyrrole Monomers: 1. Synthesis, Characterization, and Polymerization of 1-(2-Thioethyl)-Pyrrole and 3-(2-Thioethyl)-Pyrrole," *Langmuir,* 14 (11), 2970-2975, 1998.

According to one specific embodiment, the EAP active region comprises polypyrrole (PPy) doped with dodecylbenzene sulfonate (DBS) anions. When placed in contact with an electrolyte containing small mobile cations, for example, $Na^+$ cations, and when a current is passed between the EAP polypyrrole-containing active region and a counter electrode, the cations are inserted/removed upon reduction/oxidation of the polymer, leading to expansion/contraction of the same. This process may be represented by the following equation:

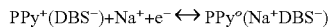

$$PPy^+(DBS^-) + Na^+ + e^- \leftrightarrow PPy^\circ(Na^+DBS^-)$$

where $Na^+$ represents a sodium ion, $e^-$ represents an electron, $PPy^+$ represents the oxidized state of the polypyrrole, $PPy^\circ$ represents the reduced state of the polymer, and species are enclosed in parentheses to indicate that they are incorporated into the polymer. In this case the sodium ions are supplied by the electrolyte that is in contact with the electroactive polymer member. Specifically, when the EAP is oxidized, the positive charges on the backbone are at least partially compensated by the $DBS^-$ anions present within the polymer. Upon reduction of the polymer, however, the immobile $DBS^-$ ions cannot exit the polymer to maintain charge neutrality, so the smaller, more mobile, $Na^+$ ions enter the polymer, expanding the volume of the same. Upon re-oxidation, the $Na^+$ ions again exit the polymer into the electrolyte, reducing the volume of the polymer.

Furthermore, networks of conductive polymers may also be employed. For example, it has been known to polymerize pyrrole in electroactive polymer networks such as poly(vinylchloride), poly(vinyl alcohol), NAFION®, a perfluorinated polymer that contains small proportions of sulfonic or carboxylic ionic functional groups., available from E.I. DuPont Co., Inc. of Wilmington, Del.

Electroactive polymers are also discussed in detail in commonly assigned copending U.S. Patent Publication No. 2005/0165439, the entire content of which is incorporated by reference herein.

The actuators according to the invention may be provided in an essentially infinite array of configurations as desired, including planar actuator configurations (e.g., with planar active members and counter-electrodes), cylindrical actuator configurations (e.g., see the actuator illustrated in FIG. 1), and so forth.

EAP-containing active regions may be provided that either expand or contract when an applied voltage of appropriate value is interrupted depending, for example, upon the selection of the EAP, dopant, and electrolyte. This can include dimensional changes in length, width, depth or combination thereof depending on the composition and configuration of the EAP actuator and how it may be disposed on a substrate, for example.

As part of a failsafe mechanism for the devices of the present invention, it may be beneficial to select actuators that are of a type that relax in the event that power is interrupted.

Additional information regarding EAP actuators, their design considerations, and the materials and components that may be employed therein, may be found, for example, in E. W. H. Jager, E. Smela, O. Inganais, "Microfabricating Conjugated Polymer Actuators," *Science,* 290, 1540-1545, 2000; E. Smela, M. Kallenbach, and J. Holdenried, "Electrochemically Driven Polypyrrole Bilayers for Moving and Positioning Bulk Micromachined Silicon Plates," *J. Microelectromechanical Systems,* 8(4), 373-383, 1999; U.S. Pat. No. 6,249,076, assigned to Massachusetts Institute of Technology, and *Proceedings of the SPIE,* Vol. 4329 (2001) entitled "Smart Structures and Materials 2001: Electroactive Polymer and Actuator Devices (see, e.g., Madden et al, "Polypyrrole actuators: modeling and performance," at pp. 72-83), each of which is hereby incorporated by reference in its entirety.

In certain other embodiments, the medical devices of the present invention are actuated, at least in part, using materials involving piezoelectric, electrostrictive, and/or Maxwell stresses.

In at least one embodiment the Electroactive Polymer Radiopaque Marker (hereinafter EAP RO Marker) 10 assists in the proper placement, and the identification of the rotational orientation, axial position etc. of an implantable medical device, such as a stent, stent-graft, vena cava filter, distal protection device, or the like. The EAP RO Marker 10 may also allow for indication of the proper rotational or axial orientation of a delivery device, such as a catheter.

FIGS. 2-22 show some embodiments of an EAP RO Marker device 10. In the embodiments shown, the EAP RO Marker 10 is arranged to allow for a determination of the orientation of the medical device with respect to the surrounding environment. EAP RO Marker 10 is mounted to the surface of a region of a medical device such as a catheter 18, or may be partially or fully recessed beneath a region of the surface of the medical device.

In some embodiments, the EAP RO Marker 10 is viewable, after insertion into a bodily lumen, through an imaging device such as a fluoroscope, X-ray, or an MRI system. EAP RO Marker 10 may comprise radiopaque elements 12.

In some embodiments, radiopaque elements 12 may be any suitable radiopaque material, such as barium, bismuth, tungsten, gold, titanium, iridium, platinum, palladium, silver, rhenium, tantalum, niobium, molybdenum, rhodium, hafnium or alloys or composites of these materials. And others, such as disclosed in U.S. Pat. No. 6,315,790, incorporated herein by reference.

In some embodiments, the EAP RO Marker may include materials suitable for use in an MRI or MRI visible devices. Such materials include but are not necessarily limited to ferromagnetic, superparamagnetic or paramagnetic material, such as gadolinium, iron or manganese containing alloys, or gadolinium-DTPA (diethylene triamine pentaacetic acid) chelates as disclosed in U.S. Pat. No. 6,361,759, incorporated herein by reference.

In some embodiments, EAP RO Markers 10 may comprise a single composition of a radiopaque element 12. EAP RO Marker 10 may also have a plurality of sections or portions of differing radiopaque elements 12. In addition, EAP RO Markers 10 may be formed of a substrate of adjacent EAP material 50 and/or radiopaque elements 12. The radiopaque elements 12 may be bands, rods and/or particles or any combination thereof. The radiopaque elements 12 may be integral to, embedded within, disposed on, intermeshed with, woven within, or otherwise engaged or positioned proximate to EAP material 50.

In at least one embodiment, the EAP RO Markers 10 may be formed through extrusion, co-extrusion, injection molding, and/or insert molding. In some embodiments, the EAP material 50 may be deposited on an EAP RO Marker 10 through vapor deposition techniques. In other embodiments, vapor deposition of radiopaque material, which may also be conductive, may occur on the marker 10, where the vapor deposited radiopaque material functions as a main electrode for a substance such as polypyrol. In alternative embodiments, the EAP RO Marker 10 may be formed through a process utilizing pad printed radiopaque inks. In at least one embodiment, the EAP RO Marker 10 may be formed through an ink jet and/or micro-drop process. In some embodiments, the EAP RO Marker 10 having barium or other filled polymers, may be formed through an extrusion or co-extrusion process.

Various materials may be more or less visible when viewed through an imaging device. Thus, certain portions of an EAP RO Marker 10 may be more or less visible than other portions of the Marker 10.

In some embodiments, EAP RO Markers 10 may be attached to the medical device, such as a catheter system 18, using any suitable method (FIGS. 8A-10B; 17; and 19A-20B). Markers 10 may be attached to the catheter system 18 using RF energy, IR energy, UV energy, laser energy, ultrasonic energy, electrical energy, chemically, which may include the use of adhesives, mechanically including swaging, and any combination thereof. The application of energy may physically bond the material of the Marker 10 with the material of the catheter system 18. In some embodiments, the application of energy may melt only the material of the catheter 18, allowing the material of the catheter 18 to surround the Marker 10. Markers 10 may also be inserted into the catheter system 18, as the device is being formed, such as during extrusion or molding of the catheter system 18.

Figure 17:
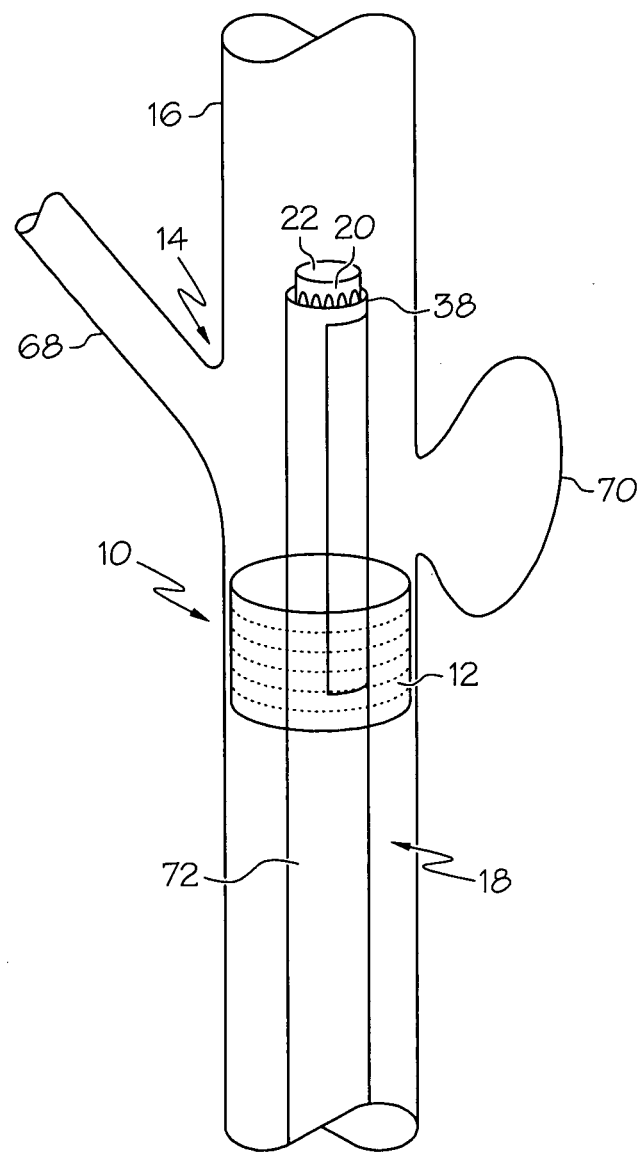
FIG. 17 shows a perspective view of an alternative medical device comprising an electroactive polymer and radiopaque framework assembly within a body lumen.

In one embodiment the catheter system 18 may comprise a catheter shaft 20 having a distal end 22 and a proximal end 24 (FIG. 17). Generally, an EAP RO Marker 10 may be disposed about the catheter shaft 20 for delivery into a bodily lumen 16.

Figure 18:
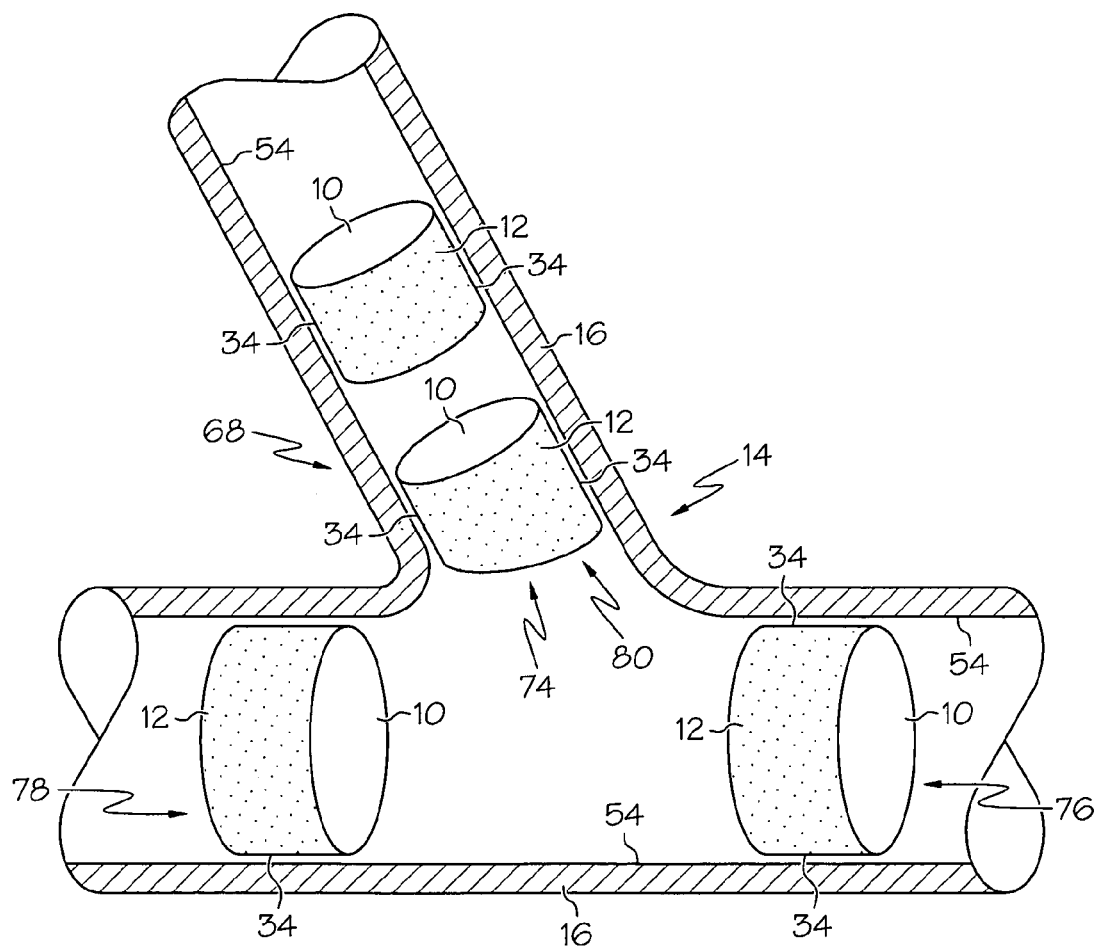
FIG. 18 shows a detail cross-sectional side view of an alternative medical device comprising an electroactive polymer and radiopaque framework assembly as disposed within a body lumen proximate a bifurcation.

In some embodiments, the EAP RO Marker 10 preferably incorporates radiopaque substances 12 to enhance visualization of a medical device proximate to a bifurcation 14 within a body lumen 16 (FIGS. 18-20B and 22A-22B). The EAP RO Marker 10 may increase or decrease in volume upon exposure to bodily fluids to absorb or diffuse anions. In one embodiment the EAP RO Marker 10 may be permanently placed within a body lumen 16 as a leave behind marker (FIG. 18). In an alternative embodiment, the EAP RO Marker 10 may be used in conjunction with a catheter system 18 to absorb ions to provide temporary visual enhancement of a body lumen 16, which may include a bifurcation area 14 (FIGS. 17; 19A-20B; and 22A-22B).

In some embodiments, the EAP RO Marker 10 may be formed of polypyrrole, nafion, polyanilene, polythiofene, and/or any other suitable material which may increase or decrease in dimension or volume due to the absorption of anions and/or cations. In general, EAP materials utilize an electrically conductive substrate and a secondary electrode to activate. An EAP RO Marker 10, exposed to applied anodic voltage, will generally expand in volume and/or dimension, due to doping, to enhance visualization of radiopaque substances 12 through a viewing device.

Figure 1B:
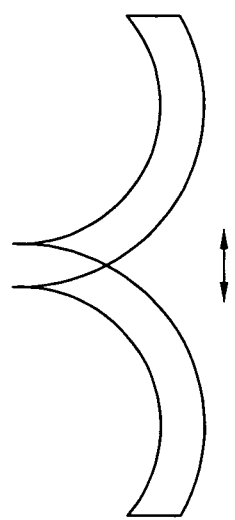
FIG. 1B shows an alternative electroactive polymer in a first arcuate state and a second arcuate state.
Figure 1A:
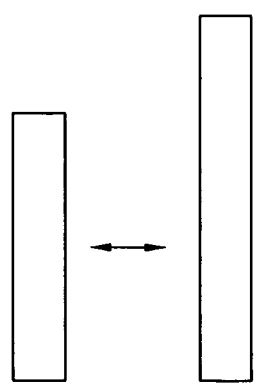
FIG. 1A shows an electroactive polymer in a first state having a length dimension and a second state having a different length dimension.

In at least one embodiment, as depicted in FIG. 1A, the exposure of anions to the EAP material may cause expansion in a longitudinal dimension. Alternatively, as depicted in FIG. 1B the exposure of anions to the EAP material may cause a change in the arcuate direction or orientation of the marker 10. The radius of the arcuate curvature may be as small as a few μm. As depicted in FIG. 1C the exposure of anions to the EAP material may cause the volume and/or length, width, and height dimension of the EAP material to enlarge.

In some embodiments, the extent of the expansion of the EAP material in either a length and/or width dimension, following exposure to anions, may vary between a few μm to several centimeters. The speed of the EAP expansion or contraction is generally dependent upon the thickness dimension selected. In some embodiments, thinner EAP materials expand and/or contract at an increased rate as compared to thicker EAP materials.

In at least one embodiment the voltage utilized to provide the desired anions or cations for implementation of a state change for the EAP RO Marker 10 into either a pre-delivery or delivery state may be less than 0.1 volt. In at least one embodiment the voltage utilized to provide the desired anions or cations for implementation of a state change for the EAP RO Marker 10 into either a pre-delivery or delivery state may be greater than 2 volts. In some embodiments, the voltage utilized to provide the desired anions or cations for implementation of a state change for the EAP RO Marker 10 into either a pre-delivery or delivery state may be between 0.1 and 2 volts.

Figure 2A:
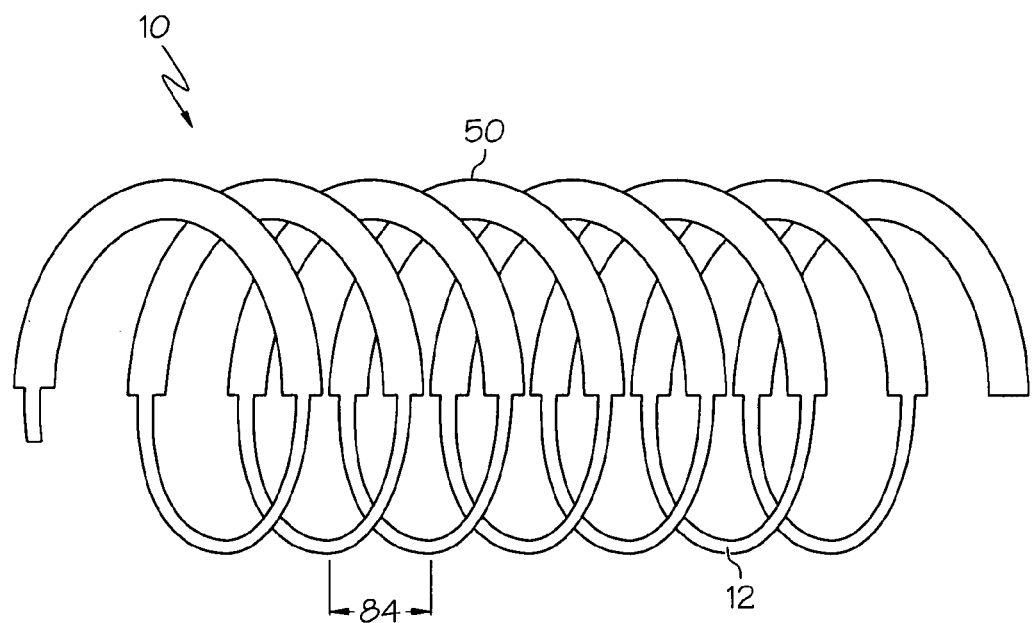
FIG. 2A shows an alternative medical device comprising an electroactive polymer and radiopaque coil framework in a delivery state.
Figure 2B:
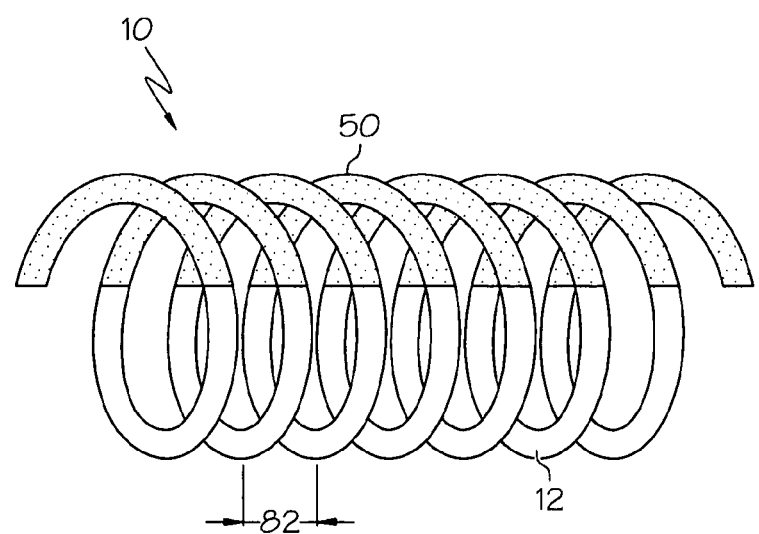
FIG. 2B shows an alternative medical device comprising an electroactive polymer and radiopaque coil framework in a pre-delivery state.

Referring to FIG. 2A and FIG. 2B, in at least one embodiment an EAP RO Marker 10 is shown for deposit within a body lumen 16. The EAP RO Marker 10 of FIG. 2A and FIG. 2B generally has the shape or configuration of a coil. Each individual rotational element of the coil may incorporate or be formed of one or more portions of the EAP material 50 and radiopaque elements 12. The EAP RO Marker 10 of FIG. 2 has a pre-delivery state as identified in FIG. 2B and a delivery state identified by FIG. 2A. The EAP RO Marker 10 transitions from the pre-delivery state of FIG. 2B to the delivery state of FIG. 2A by exposure to anions, which are absorbed by the EAP material 50. In the pre-delivery state the distance between adjacent individual coils is identified by reference numeral 82. The separation distance between adjacent individual coils following exposure to anions, is depicted by reference numeral 84. The separation distance between coils 84 for the delivery state exceeds the separation distance between coils 82 for the pre-delivery state. The change in separation distance between adjacent coils preferably assists in the visualization of the EAP RO Marker 10 during a medical procedure through the use of a Fluoroscope, X-ray, MRI, or other imaging modality. The EAP RO Marker 10 of FIGS. 2A and 2B may be delivered to a desired location within a body lumen through the use of a catheter system as known.

In some embodiments, the change in separation distance between adjacent coils provides improved flexibility for a medical device and/or EAP RO Marker 10 in a delivery configuration. The flexibility for a medical device may be adjusted or reduced by a relative change in the separation distance between adjacent coils 84, during the transition of the EAP RO Marker 10 from a delivery state to a pre-delivery configuration. A desired level of flexibility for a medical device, and/or an EAP RO Marker 10, may also be obtained during an intermediate volumetric change, which occurs between a pre-delivery configuration and a delivery state. Generally, it is undesirable to continue to incrementally alter the separation distance between adjacent coils 84, during periods when observation through an imaging device declines.

In some embodiments, the exposure of anions to the EAP RO Marker 10 causes a change in state from a pre-delivery configuration to a delivery state, at a specific time and location, to facilitate observation through an imaging modality. Once the EAP RO Marker 10 is identified as being in a desired location within a body lumen 16, the provision of anions may be terminated and/or the EAP RO Marker 10 may be exposed to cations, in order to return the EAP RO Marker 10 into a pre-delivery state or configuration. Return of the EAP RO Marker 10 to a pre-delivery state may improve the use of another catheter feature such as inflation/deflation of a balloon or other device, or improve the time, trackability, flexibility, and/or withdrawal profile for the catheter system. The EAP RO Marker 10 may alternatively be used in an intravascular ultrasound (IVUS) procedure to accurately identify the location a catheter within a body lumen.

The increase in volume of the EAP material 50 following absorption of anions, separates the individual sections of radiopaque material 12 to enlarge the area of observation within a Fluroscope, X-ray or MRI imaging device.

Figure 3A:
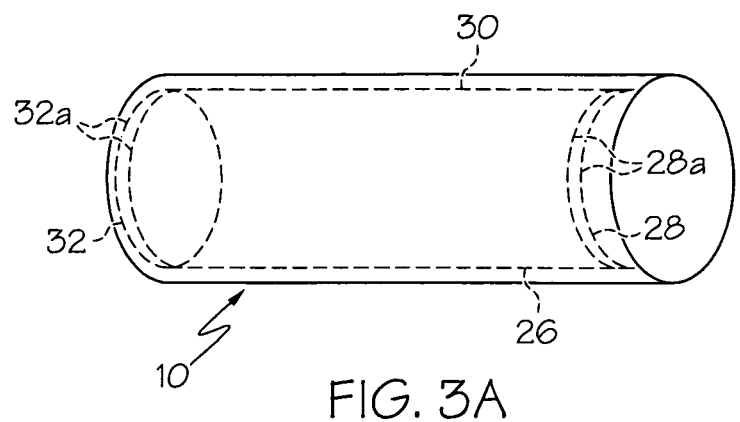
FIG. 3A shows an alternative medical device comprising an electroactive polymer and radiopaque framework assembly in a delivery state.
Figure 3B:
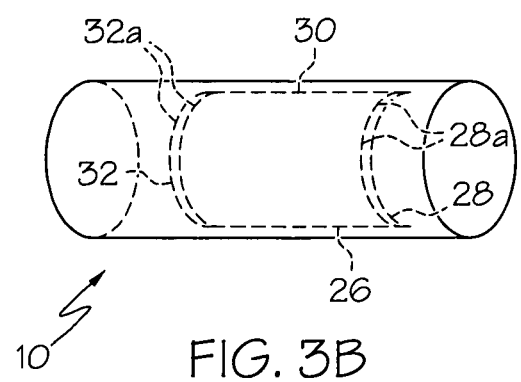
FIG. 3B shows an alternative medical device comprising an electroactive polymer and radiopaque framework assembly in a pre-delivery state.

FIGS. 3B and 3A respectively show at least one embodiment of an EAP RO Marker 10 in a first contracted or pre-delivery state and a second expanded or delivery state. The EAP RO Marker 10 may incorporate a first portion 26 of radiopaque elements extending along the length of the EAP RO Marker 10, and a second portion 28 extending about a radial arc or circumferential portion of the EAP RO Marker 10. The Marker 10 may further incorporate a third portion 30 extending along the length of the EAP RO Marker 10, and a fourth portion 32 extending about a radial arc or circumferential portion of the implantable EAP RO Marker 10.

In some embodiments, the arcuate portions 28, 32 of the EAP RO Marker 10 may comprise a plurality of arcuate elements 28a, 32a. Arcuate elements 28a, 32a may be arranged in a generally linear, single file path, or may have overlapping portions. Overlapping portions may allow the arcuate sections 28, 32 to be more visible when viewed through an imaging device. Further, as the EAP RO Marker 10 expands, arcuate elements 28a, 32a may displace with respect to one another as the diameter of the implantable EAP RO Marker 10 grows. Thus, an arcuate section 28, 32 comprising arcuate elements 28a, 32a may allow for expansion of an implantable EAP RO Marker 10 for enhanced visualization within a viewing device.

In some embodiments, individual segments of radiopaque elements may be integral to, intermeshed with, and/or impregnated within EAP RO Marker 10. The radiopaque elements may further be incorporated within the interior of a side wall 34 of an EAP RO Marker 10. (FIG. 4A)

In some embodiments, the radiopaque elements 12 may be combined and mixed for uniform dispersion within the EAP material 50. Following mixing, EAP material 50 may be extruded or cast into an EAP RO Marker 10. Alternatively, an EAP RO Marker 10 may be impregnated with radiopaque elements 12 following the formation of the desired shape for the EAP RO Marker 10.

In some embodiments, upon delivery and separation from a catheter system 18, it is anticipated that existing bodily fluids may provide the desired source of anions for the EAP RO Marker 10 to maintain a delivery configuration. Following delivery of the Marker 10, the radiopaque elements 12 function to provide enhanced visualization of the geometric orientation of a lumen, or lumen bifurcation, during a medical procedure.

Figure 4A:
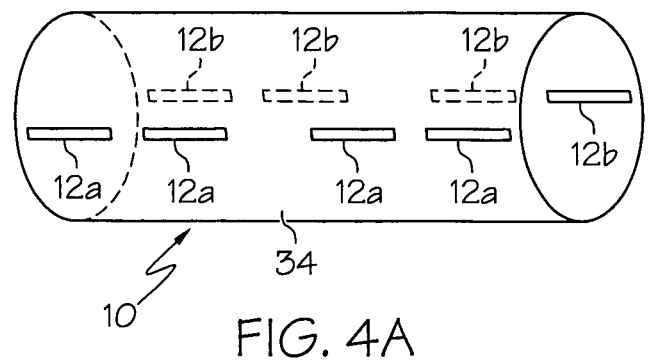
FIG. 4A shows an alternative medical device comprising an electroactive polymer and radiopaque framework assembly in a delivery state.
Figure 4B:
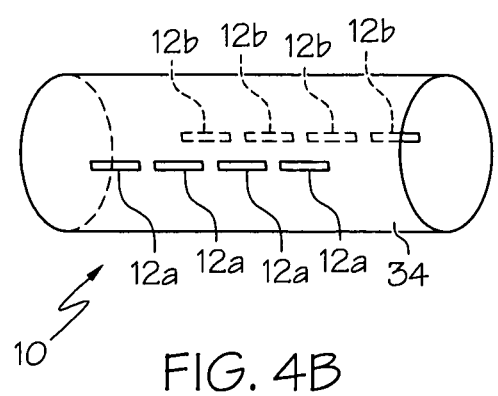
FIG. 4B shows an alternative medical device comprising an electroactive polymer and radiopaque framework assembly in a pre-delivery state.

FIGS. 4B and 4A show at least one embodiment of EAP RO Marker 10 comprising a plurality of first radiopaque elements 12a and a plurality of second radiopaque elements 12b. Radiopaque elements 12a, 12b in this embodiment do not span the entire length of the implantable EAP RO Marker 10. Radiopaque elements 12a, 12b may be separated from each other in order to allow for a shift in positioning of the radiopaque elements 12 during expansion of the EAP RO Marker 10. FIG. 4B depicts the EAP RO Marker 10 prior to absorption of anions in a first compacted pre-delivery configuration. In FIG. 4B the separation distance between adjacent radiopaque elements 12 is slightly reduced as compared to FIG. 4A. FIG. 4A depicts the EAP RO Marker 10 following absorption of anions in a second expanded delivery configuration.

In some embodiments, the separation of adjacent radiopaque elements 12 from each other facilitates observation through use of a viewing device as previously discussed. In at least one embodiment, the radiopaque elements 12b and 12a are of substantially similar size between FIGS. 4B and 4A. As depicted in FIGS. 4A and 4B the radiopaque elements 12a, 12b may be positioned in a linear orientation normal to the longitudinal axis of the EAP RO Marker 10. In alternative embodiments, the radiopaque elements 12a, 12b may be located distal or perpendicular to the longitudinal axis of the EAP RO Marker 10, or may be spiral, or may be oriented in any other desired configuration, network, and/or framework.

In one embodiment, it is anticipated that during a medical delivery procedure, the EAP RO Marker 10 of FIG. 4B will be exposed to cations. The cations function to retain the EAP RO Marker 10 in a compacted first pre-delivery state. In some embodiments, when the EAP RO Marker 10 is positioned at a desired location within a body lumen, such as adjacent to a vessel bifurcation, the provision of the cations may be terminated. In some embodiments, the EAP RO Marker 10 may then be exposed to anions from an electrical source, or through contact with bodily fluids, and/or a combination of both anions from an electrical source and anions from bodily fluid, to assist in the absorption and transition of the EAP RO Marker 10 from a pre-delivery state to a delivery state. It is anticipated that the absorption of anions and the expansion of the EAP RO Marker 10 will continue until such time as the side wall 34 is frictionally engaged to the interior of a body lumen 16.

Figure 5A:
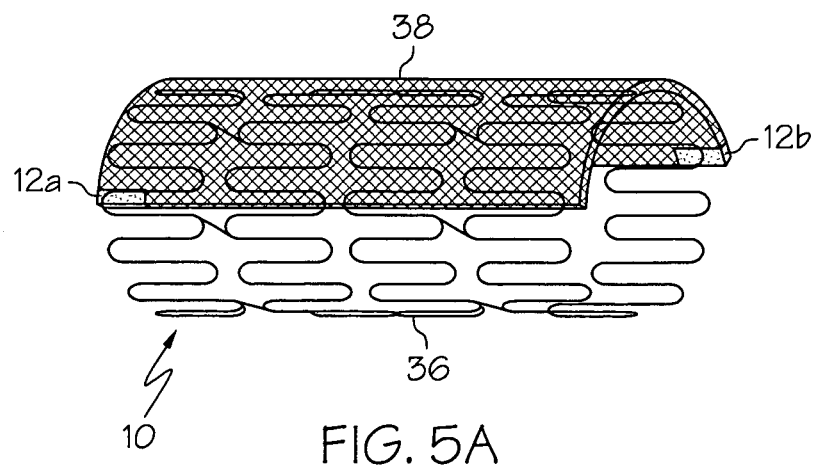
FIG. 5A shows an alternative medical device comprising an electroactive polymer and radiopaque framework assembly in a delivery state.
Figure 5B:
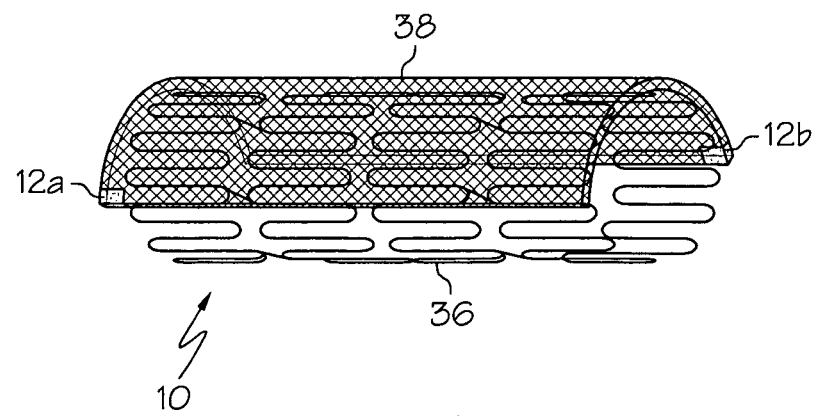
FIG. 5B shows an alternative medical device comprising an electroactive polymer and radiopaque framework assembly in a pre-delivery state.

In at least one embodiment, FIGS. 5B and 5A show an implantable medical device 36 comprising at least one EAP RO Marker 10 in the configuration of a framework, and/or substrate. Each EAP RO Marker 10 may include a first radiopaque element 12a and a second radiopaque element 12b. The individual radiopaque elements 12a, 12b are shown near the edges. In other embodiments, a first individual radiopaque element 12a may be placed to correspond to the midpoint of a marker 10. In some embodiments, the first individual radiopaque element 12a may be 180° away from the second individual radiopaque element 12b, or placed directly across the implantable medical device 36.

In at least one embodiment, as shown in FIG. 5B the implantable medical device 36 comprises an EAP RO Marker 10 in a compacted pre-delivery first state. FIG. 5A depicts implantable medical device 36 comprising at least one EAP RO Marker 10 in an expanded delivery state.

Figure 6A:
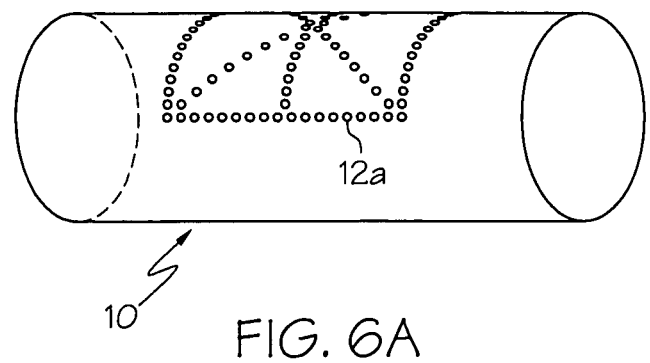
FIG. 6A shows an alternative medical device comprising an electroactive polymer and radiopaque framework assembly in a delivery state.
Figure 6B:
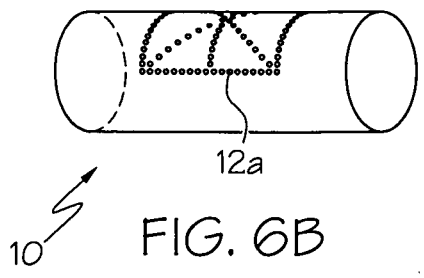
FIG. 6B shows an alternative medical device comprising an electroactive polymer and radiopaque framework assembly in a pre-delivery state.

Referring to FIGS. 6B and 6A in at least one embodiment, a plurality of individual radiopaque elements 12a may collectively comprise a pattern as incorporated into EAP RO Marker 10. Individual radiopaque elements 12a may be incorporated into the EAP RO Marker 10 using any suitable method. Individual radiopaque elements 12a may follow any desired framework or substrate, and may form a straight, arcuate, spiral, sinuous, or serpentine path. Individual radiopaque elements 12a may be positioned to form a symbol when viewed during use of an imaging device at a correct rotational orientation.

Figure 7A:
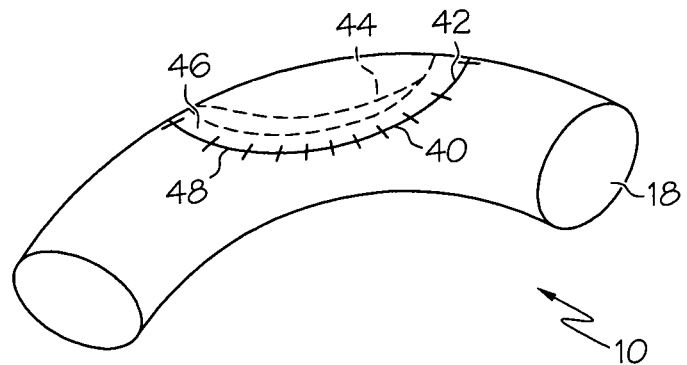
FIG. 7A shows an alternative medical device comprising an electroactive polymer and radiopaque framework assembly in a delivery state.
Figure 7B:
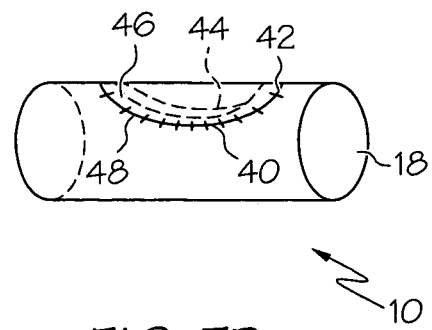
FIG. 7B shows an alternative medical device comprising an electroactive polymer and radiopaque framework assembly in a pre-delivery state.

In at least one embodiment, an EAP RO Marker 10 comprises a segmented radiopaque element as shown in FIGS. 7B and 7A. A segmented radiopaque element may include a collection of sections that are generally lengthwise 40, 44 and a collection of sections which may be arcuate 42, 46. Generally lengthwise sections 40, 44 may be substantially parallel to the longitudinal axis of the catheter system 18. A segmented radiopaque element may further include intermediate sections 48 which are not parallel to the longitudinal axis of the catheter system 18.

In some embodiments, the path of the segmented radiopaque elements may be arranged to generally indicate the edges of a graft portion of an implantable medical device. The segmented radiopaque elements may indicate the rotational position of a graft portion under fluoroscopy, X-ray, MRI, or other imaging device.

In at least one embodiment as depicted in FIG. 7B, an alternative EAP RO Marker 10 in a first compacted pre-delivery state is shown. FIG. 7A shows an alternative EAP RO Marker 10 in a second expanded delivery state following the absorption of anions.

Figure 8A:
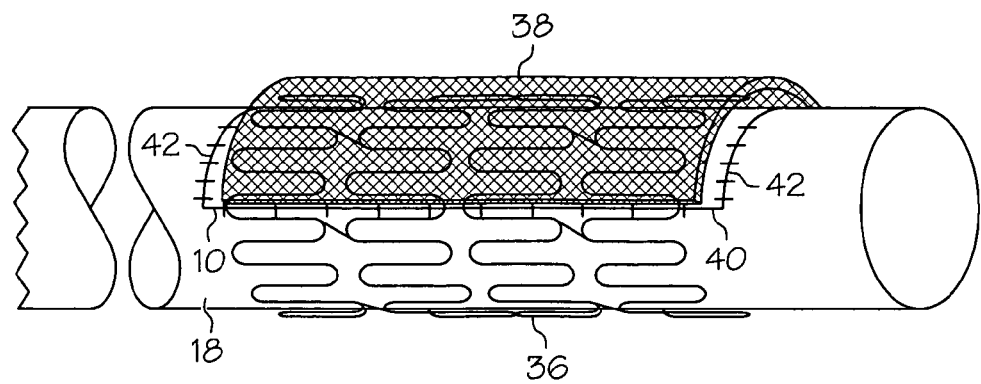
FIG. 8A shows an alternative medical device including an alternative electroactive polymer and radiopaque framework and catheter assembly in a delivery state.
Figure 8B:
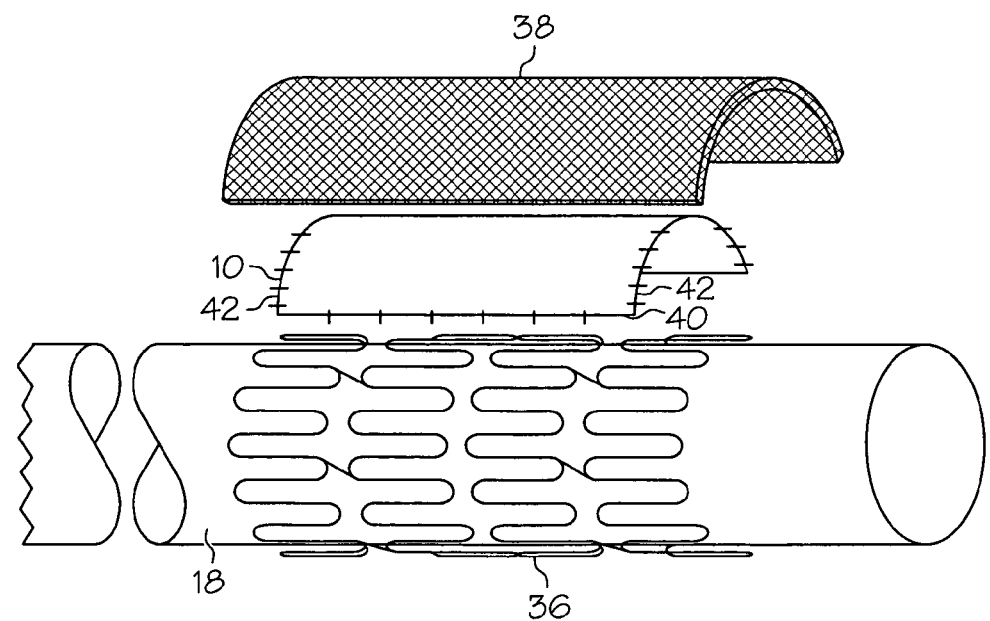
FIG. 8B is an exploded view of an alternative medical device comprising an electroactive polymer and radiopaque framework and catheter assembly of FIG. 8A in a pre-delivery state.
Figure 9A:
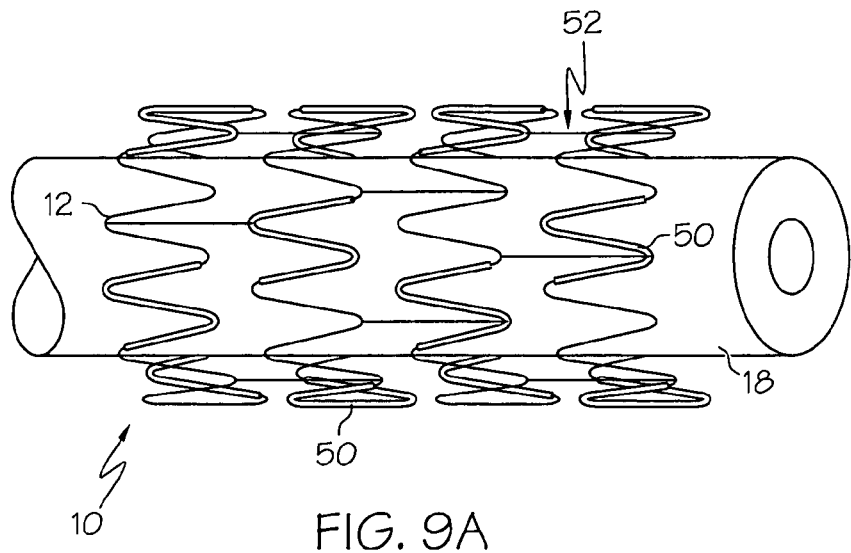
FIG. 9A shows an alternative medical device comprising an electroactive polymer and radiopaque framework assembly in a delivery state.
Figure 9B:
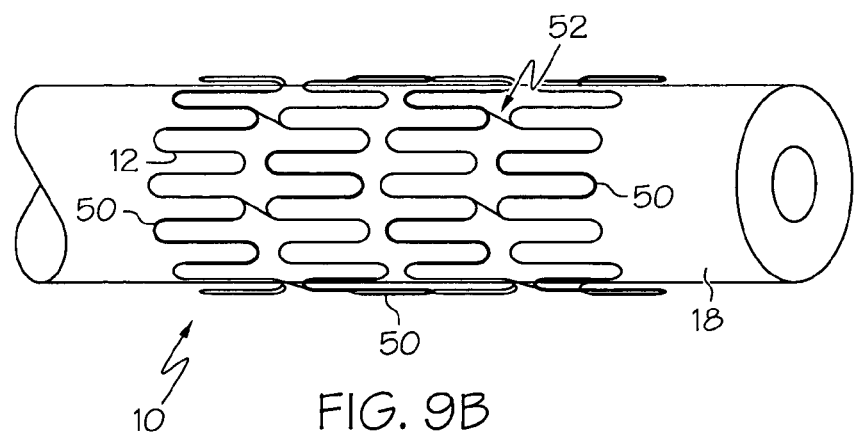
FIG. 9B shows an alternative medical device comprising an electroactive polymer and radiopaque framework assembly in a pre-delivery state.

In at least one embodiment, a medical device comprising a catheter system 18 having an EAP RO Marker 10, and an implantable medical device 36, such as a stent or stent-graft, mounted upon the catheter system 18, is shown in FIGS. 8A-8B. A stent 36 may include a graft portion 38, or other covering, over a portion of the stent 36. Suitable coverings include nylon, collagen, PTFE and expanded PTFE, polyethylene terephthalate and Kevlar, or any of the materials disclosed in U.S. Pat. No. 5,824,046 and U.S. Pat. No. 5,755,770 incorporated by reference herein. More generally, any known graft material may be used including synthetic polymers such as polyethylene, polypropylene, polyurethane, polyglycolic acid, polyesters, polyimides, their mixtures, blends and copolymers. Desirably, the graft portion 38 is located in relation to the EAP RO Marker 10 such that the EAP RO Marker 10 may be used to correctly position the graft 38 within a body lumen 16.

In some embodiments, the size and location of the EAP RO Markers 10 may be adjusted for use within a particular application. For example, segmented lengthwise portions 40 of radiopaque elements may be substantially coextensive with an implantable medical device 36, or may extend slightly beyond the ends of an implantable medical device 36. Further, segmented lengthwise portions 40 of radiopaque elements may be placed near the edges of a graft portion 38. Segmented portions 42 of radiopaque elements may have an arc length similar to the arc length of a graft portion 38. In some embodiments, the EAP RO Marker 10 represents the size, location, and boundaries of a medical device such as a graft 38, when viewed with an imaging device, to facilitate the accuracy of the position of the medical device in relation to a vessel stenosis. The change from a pre-delivery configuration into a delivery state facilitates the observation of an EAP RO Marker 10 through the imaging device.

In some embodiments, the EAP RO Markers 10 may incorporate members 50 which may be configured into a pattern 52 or substrate of interconnected segments such as shown in FIGS. 9A and 9B. The pattern 52, or substrate, may have any configuration, shape, or design. In one embodiment, the catheter system 18 includes a pattern 52, or substrate of radiopaque material members 12 and EAP members 50 disposed over the catheter 18. The resulting composite EAP RO marker 10 comprises a plurality of individual strands/sections of radiopaque members 12 and EAP members 50 corresponding to the longitudinal length of the pattern 52. In at least one embodiment, the configuration, shape or design of the EAP RO Members 50 comprising patterns 52, when viewed with an imaging device, facilitates the accuracy of the position of a medical device in relation to a body lumen. The change from a pre-delivery configuration into a delivery state facilitates the observation of an EAP RO Marker 10 through an imaging device.

In some embodiments, each individual band member may incorporate one or more separate portions of EAP material 50 and radiopaque material 12. Adjacent band members may be connected to each other to form the pattern 52, or substrate.

In at least one embodiment, FIG. 9B depicts the EAP RO Marker 10 in a first per-delivery configuration as engaged to a catheter system 18 for introduction into a body lumen 16. FIG. 9A depicts the EAP RO Marker 10 in a second expanded delivery configuration following absorption of anions. After the EAP RO Marker 10 has acquired a delivery configuration the catheter system 18 may be withdrawn from a body lumen 16.

Figure 10A:
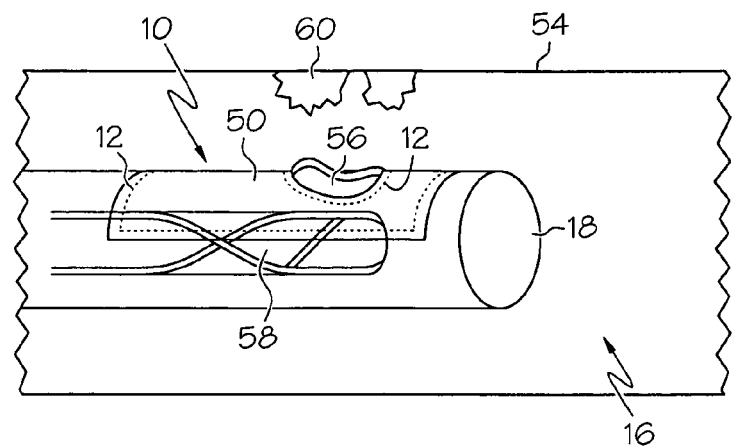
FIG. 10A shows an alternative medical comprising an electroactive polymer and radiopaque framework assembly in an activated state.
Figure 10B:
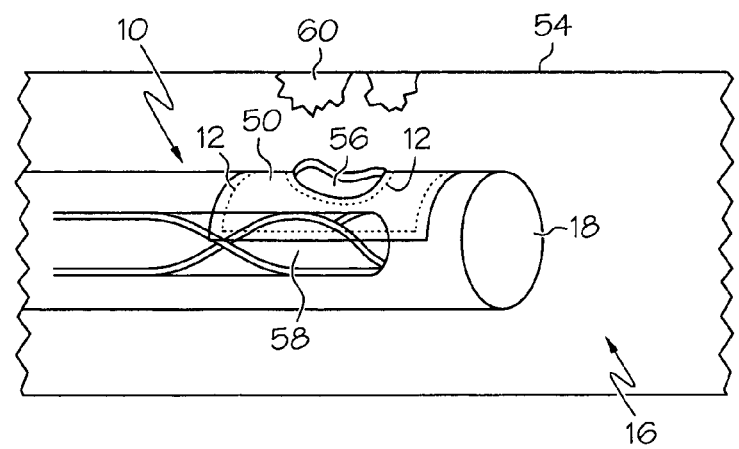
FIG. 10B shows an alternative medical device comprising an electroactive polymer and radiopaque framework assembly in a pre-activation state.

Referring to FIGS. 10A and 10B, in at least one embodiment an EAP RO Marker 10 may comprise a catheter system 18 disposed within a body lumen 16 having a circumferential wall 54. The catheter system 18 may further include an aperture or port 56. Desirably, the port 56 may be positioned such that orientation and placement of the port 56 may be determined via the image of the EAP RO Marker 10 upon an imaging device. It is also within the scope of the invention for port 56 to include a plurality of radiopaque marker elements 12 adjacent the rim of the port 56. The radiopaque marker elements 12 may be of any suitable type.

In at least one embodiment, the catheter system 18 may further include a rotational ablation device 58, and the catheter system 18 may be used to remove plaque or other deposits 60 from a vessel wall as disclosed in U.S. Pat. No. 6,179,851, the entire disclosure of which is incorporated by reference herein in its entirety.

In at least one embodiment, the EAP RO Marker 10 is also directed to a method of using an inventive medical device in an atherectomy procedure. The catheter system 18 may be inserted into a body lumen 16 and maneuvered to a vessel location having a deposit 60, such as plaque, a clot, or other type of thrombus. An imaging device may be used to view a EAP RO Marker 10 to facilitate positioning of the catheter system 18 with the port 56 immediately adjacent to a deposit 60. As the catheter system 18 is moved in the direction of the deposit 60, rotation ablation device 58 may remove portions of the deposit 60 from the vessel wall 54. The portions that have been removed may then enter the port 56. Desirably, the removed deposit 60 material may be carried away within the catheter system 18.

In at least one embodiment, FIG. 10B depicts the EAP RO Marker 10 in a first pre-delivery state. FIG. 10A depicts the EAP RO Marker 10 in a second delivery state following exposure to, and absorption of, anions. The radiopaque marker elements 12, adjacent to the rim of port 56, in conjunction with the EAP members, when viewed through an imaging device, facilitates observation and positioning of a medical device proximate to a deposit 60, plaque, clot, or thrombus, particularly when the EAP RO Marker 10 is viewed prior to, during, and following a transition between a delivery and pre-delivery state.

Figure 11A:
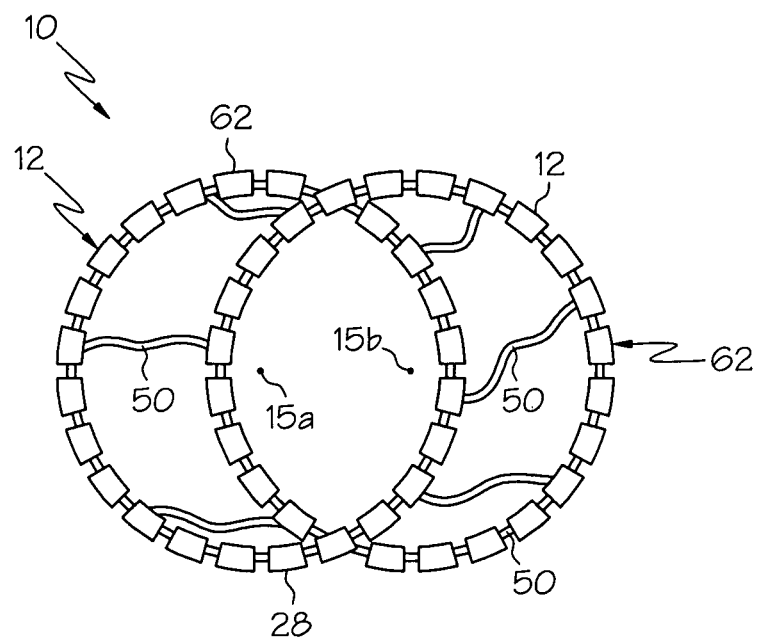
FIG. 11A shows an alternative medical device comprising an electroactive polymer and radiopaque framework assembly in an activated state.
Figure 11B:
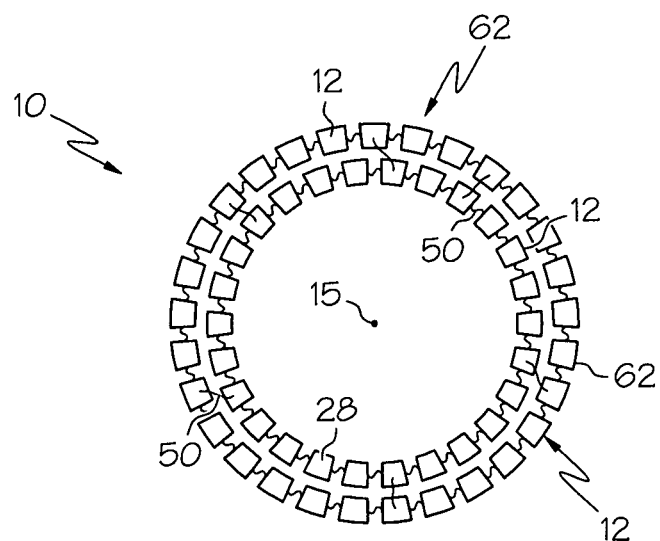
FIG. 11B shows an alternative medical device comprising an electroactive polymer and radiopaque framework assembly in a pre-activation state.

As may be seen in at least one alternative embodiment as depicted in FIGS. 11A and 11B, the EAP RO Marker 10 may be formed of one or more rings 62. In this embodiment, a plurality of radiopaque elements 12 are positioned adjacent to each other to form a portion of each ring 62. EAP materials/members 50 are preferably in contact with, and are disposed between, adjacent radiopaque elements 12. In addition, EAP material/members 50 may also extend between adjacent rings 62.

Referring to FIG. 11B, each of the adjacent radiopaque elements 12 and rings 62 are compacted relative to one-another, to define a first compact pre-delivery state. Following exposure of the EAP RO Marker 10 to anions, the EAP members 50 preferably expand separating the adjacent radiopaque elements 12 from each other, and spatially separating the rings 62 from each. The delivery state for the EAP RO Marker 10 is depicted in FIG. 11A. The radiopaque marker elements 12 of the ring 62, in conjunction with the EAP material/members 50, when viewed through an imaging device, facilitates observation and positioning of a medical device within a body lumen, particularly when the EAP RO Marker 10 is viewed prior to, during, and following a transition between a pre-delivery and delivery state. The accurate positioning of a medical device within a body lumen is improved through the use of the EAP RO Markers 10.

Figure 12:
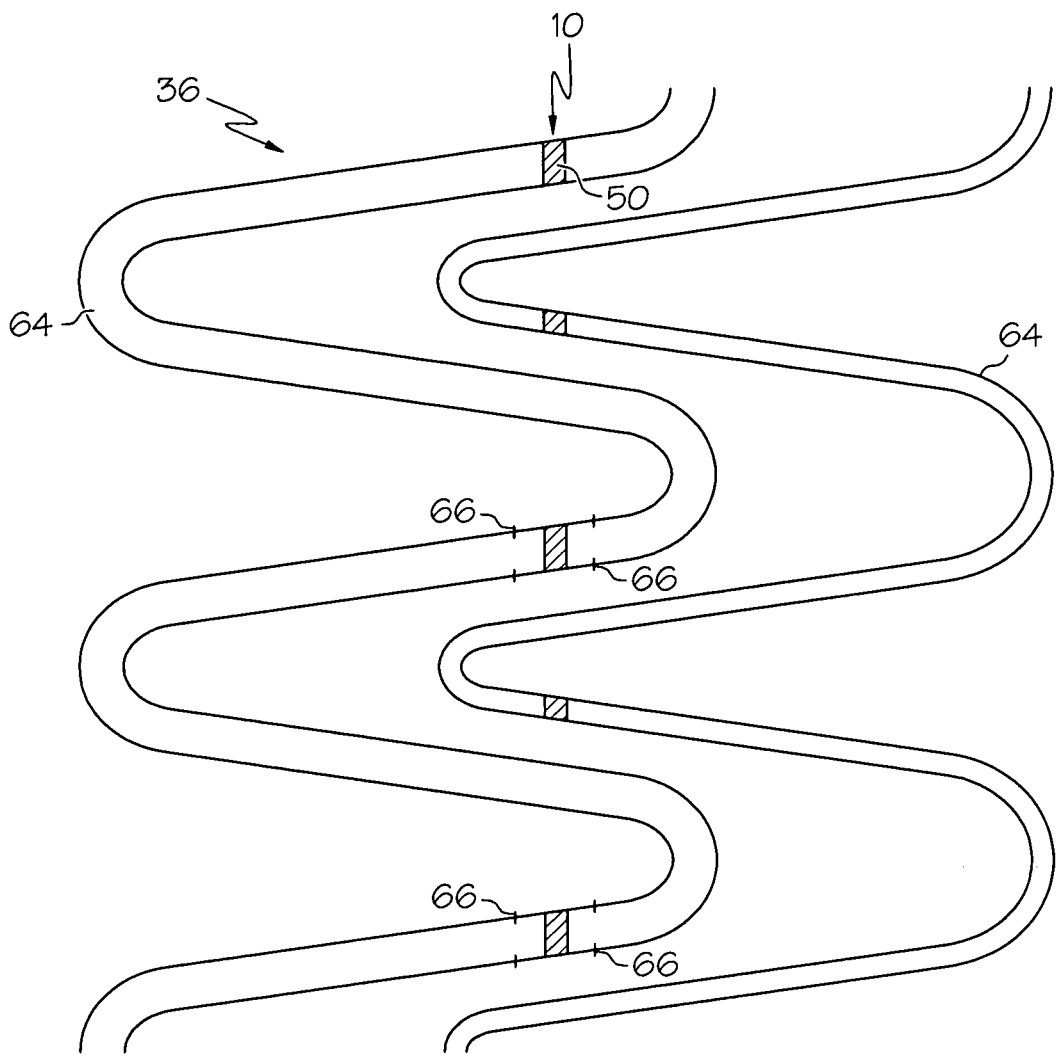
FIG. 12 shows an alternative medical device comprising an electroactive polymer and radiopaque framework assembly.
Figure 14:
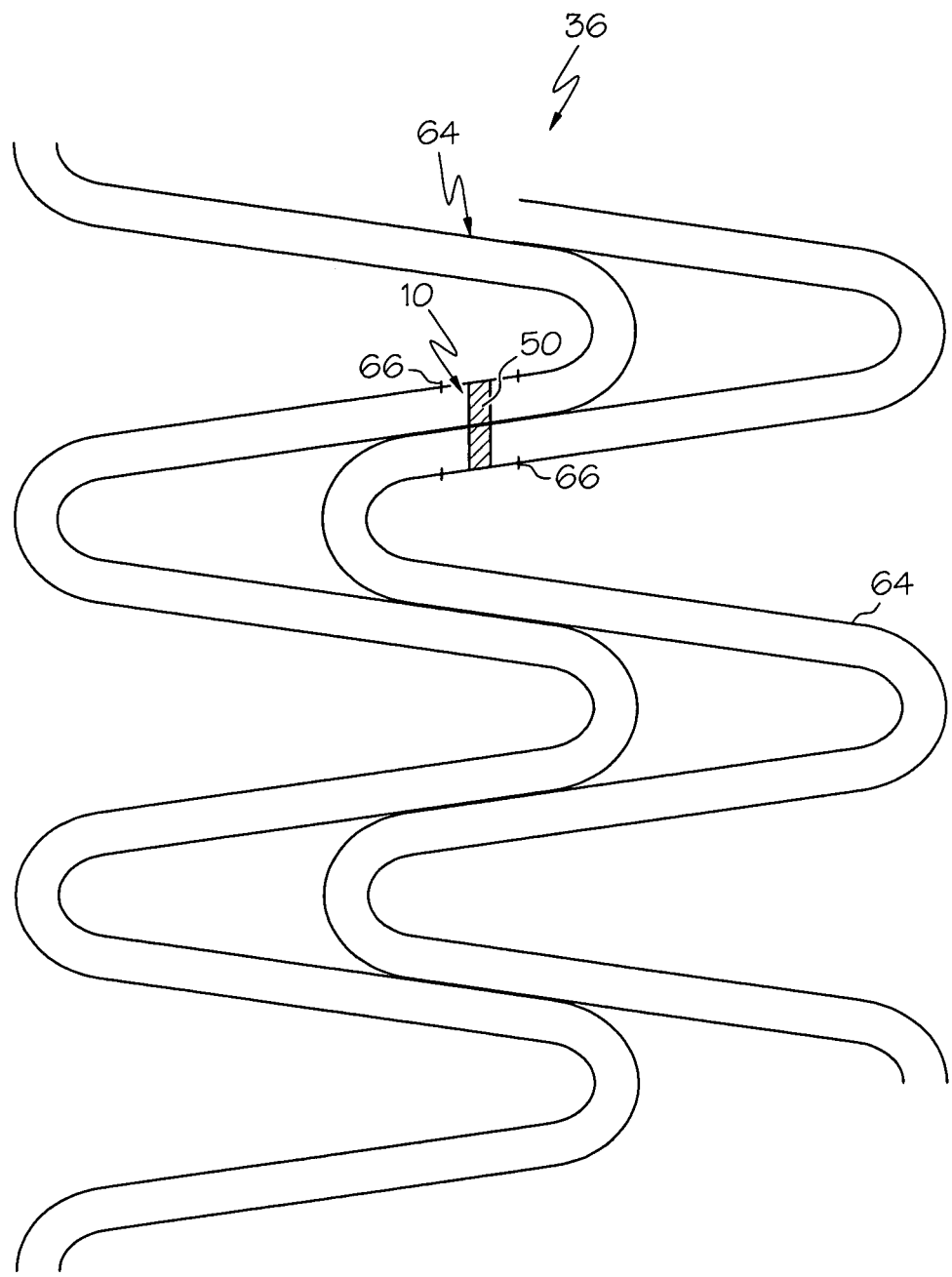
FIG. 14 shows an alternative medical device comprising an electroactive polymer and radiopaque framework assembly.

Referring to FIGS. 12 and 14, at least one embodiment of an implantable medical device 36 is depicted as comprising a plurality of serpentine elements 64. One or more EAP RO Markers 10 may disposed circumferentially about one or more of the serpentine elements 64. Each EAP RO Marker 10 is preferably formed of EAP material 50 and radiopaque elements. Exposure of the EAP RO Marker 10 to anions preferably causes the EAP material 50 to expand in volume thereby separating adjacent radiopaque elements from each other, to enhance visualization through a device such as a fluoroscope, X-ray or MRI.

Figure 13A:
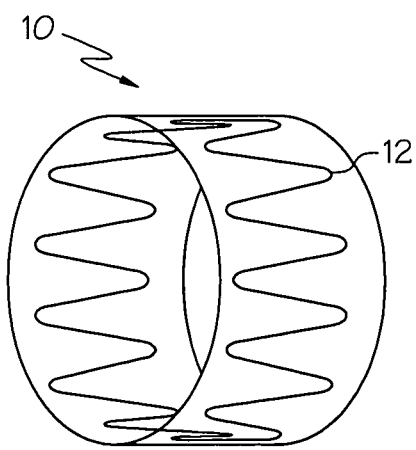
FIG. 13A shows a detail view of an alternative medical device comprising an electroactive polymer and radiopaque framework assembly in a delivery state.
Figure 13B:
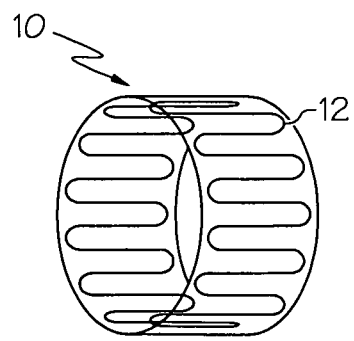
FIG. 13B shows a detail view of an alternative medical device comprising an electroactive polymer and radiopaque framework assembly in a pre-delivery state.

The expansion of individual EAP RO Marker 10 bands from a pre-delivery state to a delivery state is depicted in FIGS. 13B and 13A.

In at least one embodiment, the EAP RO Markers 10 may be slidably positioned relative to a serpentine element 64 or may be positioned for retention within a specified area on the serpentine band 64 through the use of channels and/or stops 66. (FIGS. 12 and 14.)

In at least one embodiment, as depicted in FIG. 14, adjacent serpentine elements 64 may be secured together by a single EAP RO Marker 10. In at least one embodiment, the transition of the EAP RO Marker 10, as engaged to adjacent serpentine elements, from a pre-delivery configuration and a delivery state, enhances the observation of the EAP RO Marker through an imaging device, while simultaneously permitting separation between, and/or contraction of, the relative position of the adjacent serpentine elements. In at least one embodiment, the separation between adjacent serpentine elements is desirable within a medical procedure.

Figure 15:
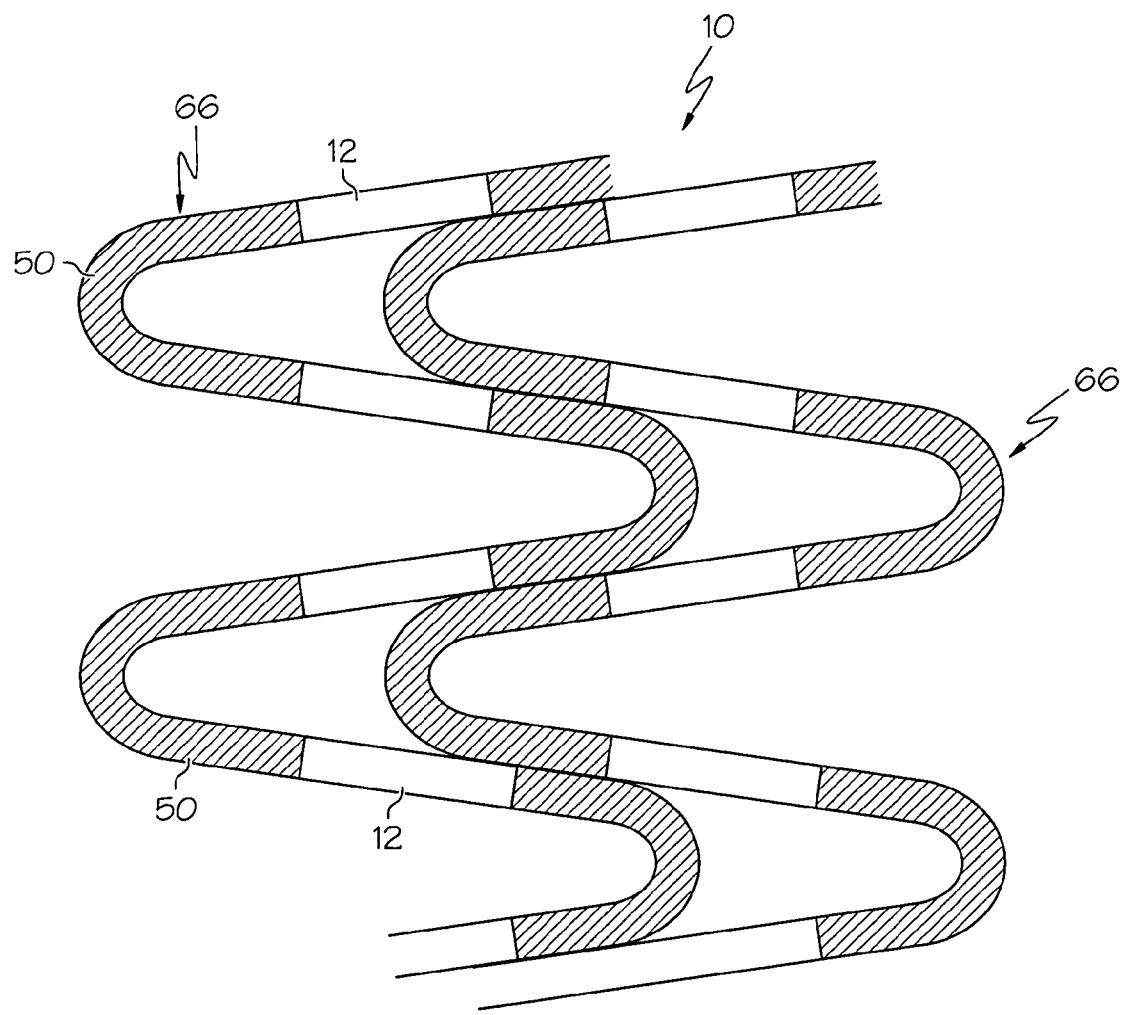
FIG. 15 shows an alternative medical device comprising an electroactive polymer and radiopaque framework assembly.
Figure 16:
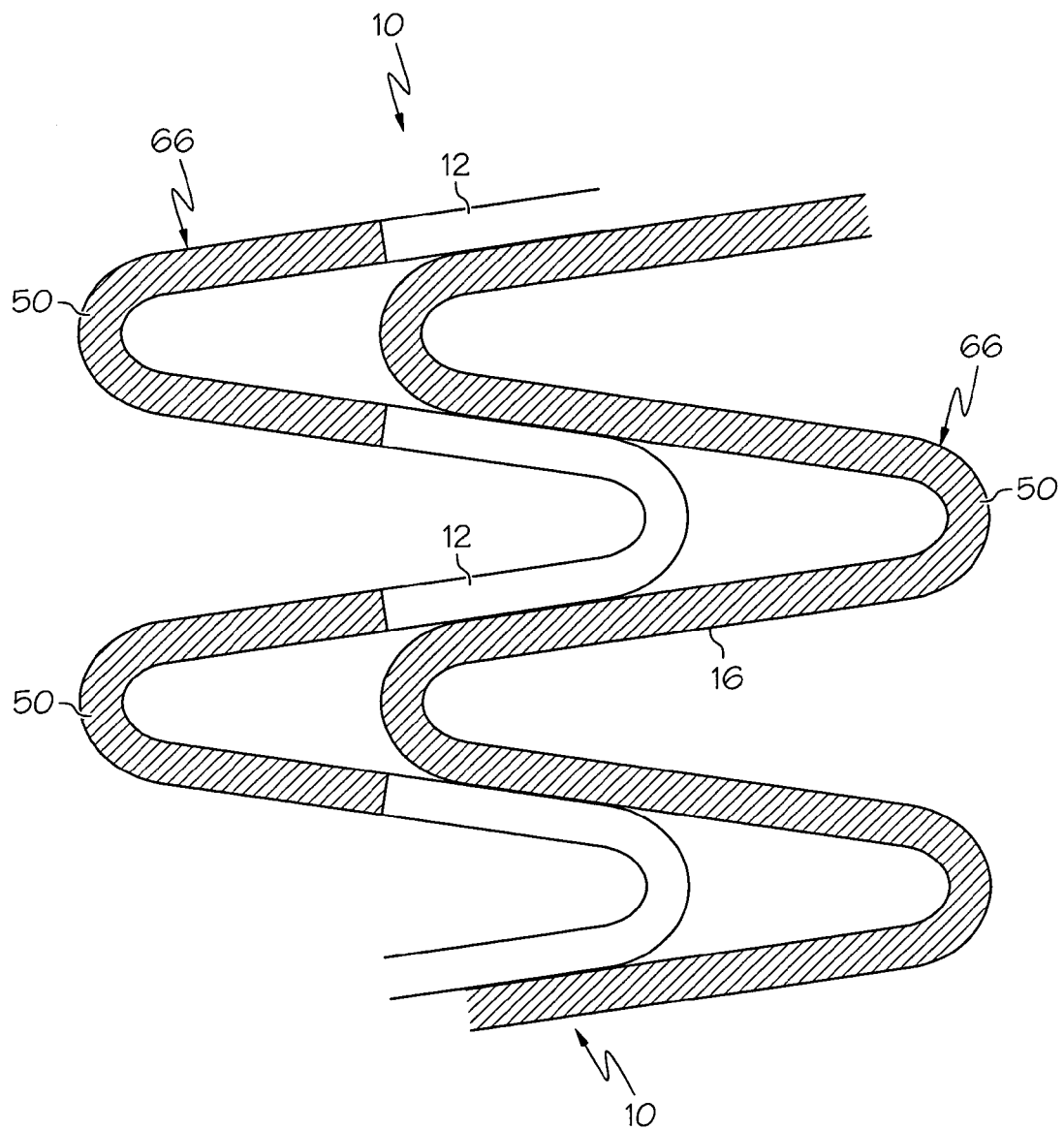
FIG. 16 shows an alternative medical device comprising an electroactive polymer and radiopaque framework assembly.

Referring to FIGS. 15 and 16, in some embodiments EAP RO Marker 10 may comprise a framework, or substrate of one or more serpentine members 66. Each of the serpentine members 66 may unite segments of EAP material 50 and radiopaque elements 12 together. The segments of EAP material 50 and radiopaque elements 12 may alternate within a particular serpentine member 66, or between adjacent serpentine members 66. The framework or substrate comprising the EAP RO Marker 10 does not require that the members 66 have any particular configuration such as serpentine, where alternatively the members 66 may be linear or any other shape as desired.

In at least one embodiment as depicted in FIG. 17, EAP RO Marker 10 is shown to be placed within a body lumen 16 adjacent a side branch 68 and an aneurysm 70. In this embodiment, the EAP RO Marker 10 is delivered through the use of a catheter system 18 having a sheath 72. The catheter system 18 may include a graft portion 38 which is arranged between the catheter shaft 20 and the sheath 72. The EAP RO Marker 10 is positioned to indicate the approximate location and rotational orientation of the graft portion 38. Thus, the EAP RO Marker 10 facilitates placement of the catheter system 18 such that the graft portion 38 may cover the aneurysm 70 without a consequential blockage of the side branch 68.

Referring to FIG. 18, in at least one embodiment, a body lumen 16 having a vessel bifurcation 14 or side branch 68 is depicted with a plurality of EAP RO Markers 10. An EAP RO Marker 10 may be deployed in the main vessel of a body lumen 16 proximate 76 to the ostium 74. Alternatively, or in combination, an EAP RO Marker 10 may be deployed in the main vessel of a body lumen 16 distal 78 to the ostium 74. Furthermore, one or more EAP RO Markers 10 may be deployed either proximal 80, or distal to, the ostium 74 and/or within the side branch 68 of the body lumen 16. Any combination of EAP RO Markers 10 may be deployed to facilitate the mapping or pre-mapping of a region of a body lumen 16 as a portion of a medical procedure.

FIG. 18, in at least one embodiment, depicts the EAP RO Markers 10 in a delivery state where a side wall 34 is preferably frictionally engaged to the interior side wall 54 of a body lumen 16. The EAP RO Markers 10 prior to deployment may be transported to a location proximate to the ostium 74 of a side branch 68 in a pre-delivery or compact state by a catheter system 18 as previously identified. It is anticipated that any of the known catheter systems 18 may be utilized in the positioning and delivery of an EAP RO Marker 10 to map or pre-map a body lumen 16 during a medical procedure.

In some embodiments, it is further anticipated that an EAP RO Marker 10 will be exposed to cations during transportation in a pre-delivery or compact state. Following the positioning of an EAP RO Marker 10 proximate to a side branch 68, exposure of anions may occur to minimize the time required for the EAP RO Marker 10 to increase in volume to the delivery configuration.

Figure 19A:
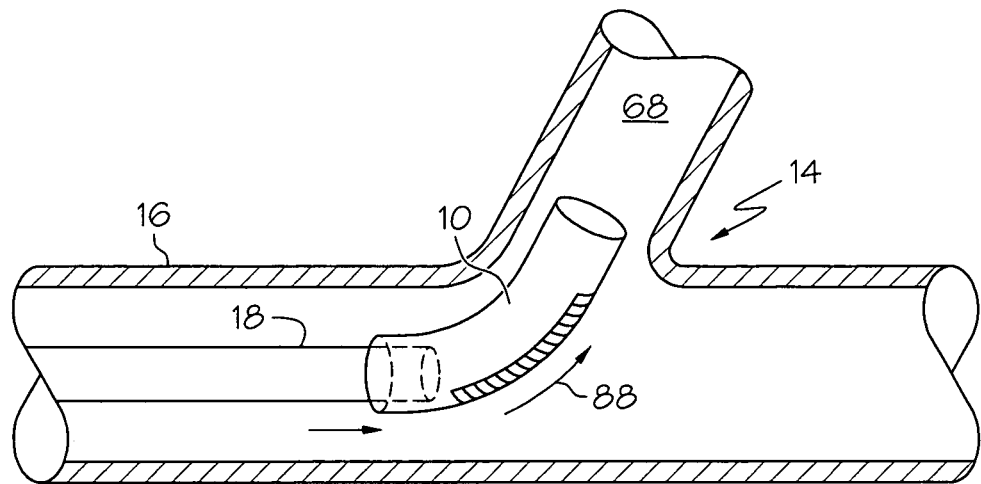
FIG. 19A shows an alternative medical device comprising an electroactive polymer and radiopaque framework assembly in a delivery state.
Figure 19B:
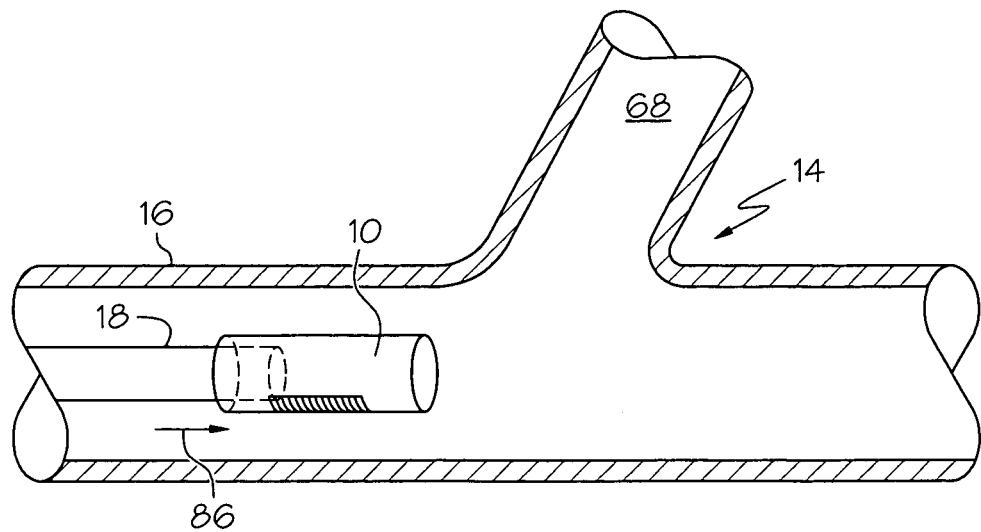
FIG. 19B shows an alternative medical device comprising an electroactive polymer and radiopaque framework assembly in a pre-delivery state.

As may be seen in FIGS. 1B and 19A-19B, in some embodiments, the EAP RO Markers 10 upon exposure to anions may arc, or change in size or volume, in a desired direction for insertion within a side branch 68 of a body lumen 16. The insertion of a catheter system 18 within a body lumen 16 is referenced by arrow 86 of FIG. 19B. Arrow 88 of FIG. 19A depicts the insertion of a catheter system 18 and EAP RO Markers 10 within a side branch 68 following exposure to anions. In some embodiments the EAP RO Markers 10 may receive asymmetrical exposure to anions to facilitate an asymmetrical expansion, arc, or a change in size or volume.

In at least one embodiment as depicted in FIGS. 19A and 19B, the catheter system 18 preferably includes an electrical element which is in electrical communication with the power source and the EAP RO Markers 10. Anions may therefore be provided to the EAP RO Markers 10 to initiate, and facilitate, the transition into an arcuate configuration for insertion into a side branch 68 of a body lumen 16. The EAP RO Markers 10 may be designed to arc in any desired direction for use in a medical procedure.

Figure 20A:
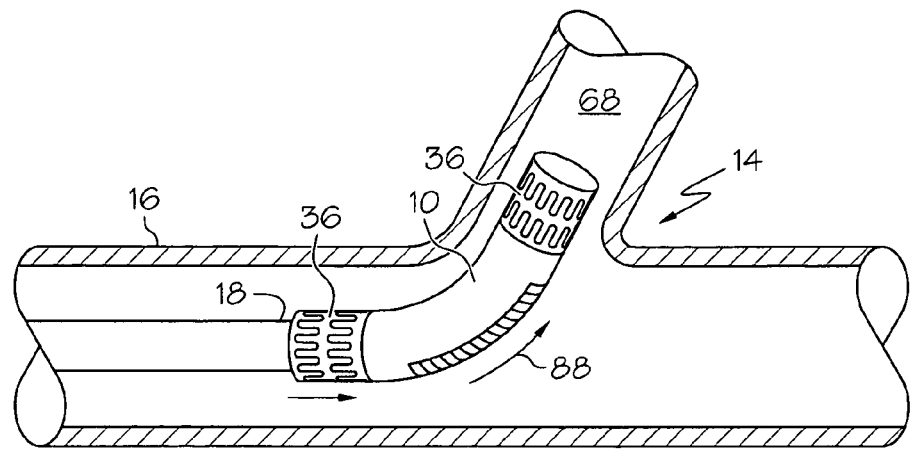
FIG. 20A shows an alternative medical device comprising an electroactive polymer and radiopaque framework assembly in a delivery state.
Figure 20B:
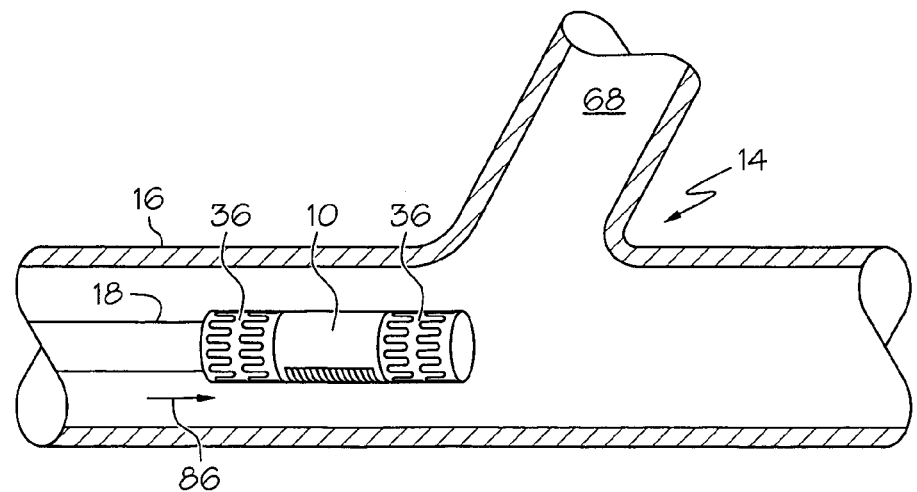
FIG. 20B shows an alternative medical device comprising an electroactive polymer and radiopaque framework assembly in a pre-delivery state.

As may be seen in at least one embodiment as depicted in FIGS. 20A-20B an implantable medical device 36 such as a stent may be engaged to either side of an EAP RO Marker 10 for insertion within a side branch 68 of a body lumen 16. Application of electrical current preferably exposes the EAP RO Marker 10 to anions, which in turn, causes the marker 10 to arc for insertion into the side branch 68 as depicted by arrow 88. The EAP RO Marker 10 preferably arcs relative to a side branch 68 and a catheter system 18 as previously described with reference to FIGS. 18A-18B. The EAP RO Markers 10 may also be used to separate implantable medical devices 36 from each other in a non-arcuate or linear direction as desired. In alternative embodiments, a medical device such as a stent may be positioned in partial or complete covering relationship over the entire EAP RO Marker 10, or a portion thereof.

Figure 21A:
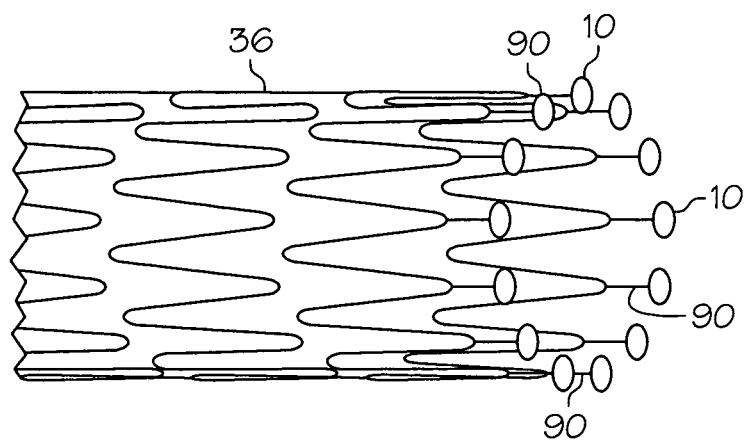
FIG. 21A shows an alternative medical device comprising an electroactive polymer and radiopaque framework assembly in a delivery state.
Figure 21B:
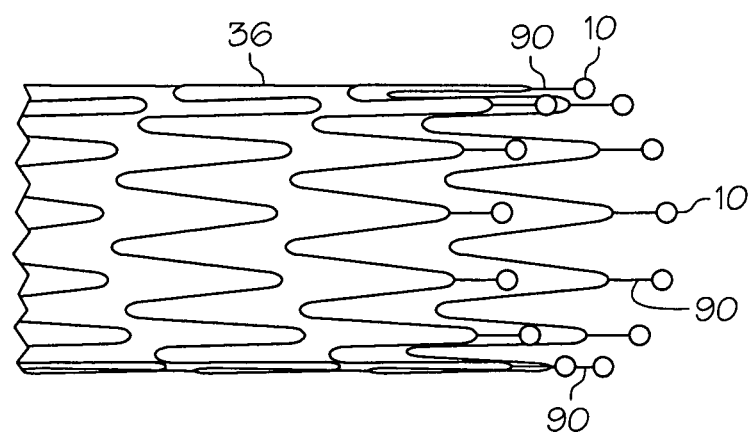
FIG. 21B shows an alternative medical device comprising an electroactive polymer and radiopaque framework assembly in a pre-delivery state.

As may be seen in at least one embodiment as depicted in FIGS. 21A and 21B an implantable medical device 36 may include receptor areas 90. An EAP RO Marker 10 is preferably engaged to each receptor area 90. The exposure of anions to the EAP RO Markers 10 cause the markers 10 to volumetrically expand into a second enlarged state as depicted in FIG. 21A. In some embodiments, the exposure of anions to the EAP RO Markers 10 may cause the Markers 10 to volumetrically expand into a second shape. The distal end of an implantable medical device 36 is therefore more readily viewable as a result of the increased volumetric area of each marker 10 through use of a fluoroscope, x-ray, MRI or other imaging device.

In some embodiments, the EAP RO Markers described herein may be formed of a composite framework or substrate of electroactive polymer and radiopaque polymer materials. Examples of radiopaque polymer materials are disclosed in U.S. Pat. Nos. 6,888,098B1; 6,746,661B2; 6,682,537B2; 6,641,606B2; 6,530,934B11; 6,514,193B2; 6,267,775B1; 6,200,338; 6,077,880; 6,059,812; 6,056,700; 6,040,408; 5,256,334; 5,024,232; 4,882,392; and 4,866,132, which are incorporated herein by reference in there entireties.

In some embodiments, the composite radiopaque and electroactive polymer material framework or substrate may be molded or extruded into any desired configuration or shape for the EAP RO Markers 10.

In some embodiments, one or more EAP RO Markers 10 may be used as leave behind mapping devices for a body lumen 16 to assist in the identification of bifurcation areas 14 during medical procedures. Alternatively, the EAP RO Markers 10 may be designed for withdrawal from a body lumen 16 upon the completion of a medical procedure.

In some embodiments, one or more EAP RO Markers 10 may be engaged to a catheter system 18 for insertion within a body lumen 16. The EAP RO Markers 10 are generally in an initial pre-delivery or compact state. The EAP RO Markers 10 as engaged to the catheter system 18 may also be in electrical communication with a source of cations to assist in the retention of the Markers 10 in a pre-delivery state or may be in electrical communication with a source of anions which are used to transition the Markers 10 from the pre-delivery state. The identical electrical pathway may alternatively be used as a conduit of anions which are used to transition the Markers I0 from the pre-delivery state to the expanded delivery state.

During some medical procedures, the relative location of the distal end 22 of the catheter system 18 and the EAP RO Markers 10 may be identified through fluoroscopy, X-ray, MRI, or other viewing procedure. At specific locations the advancement of the catheter system 18 may be temporarily suspended whereupon anions may be exposed to the EAP RO Markers 10. The EAP RO Markers 10 may then expand into a delivery state which increases the volume and/or surface area to be visualized through the use of an imaging device. A medical provider therefore may receive improved images to identify the configuration of a bifurcation 14 of the body lumen 16 to be navigated. A medical provider may then expose the EAP RO Markers 10 to cations to return Markers 10 to a pre-delivery state for further insertion within a body lumen 16 in conjunction with the catheter system 18. The provision of anions and/or cations to the EAP RO Markers 10 assist a medical provider in the exact positioning of the Markers 10 within a body lumen.

In some embodiments, once EAP RO Markers 10 have been placed at a desired location, the EAP RO Markers 10 may be separated or detached from the catheter system 18 to function as leave behind markers for mapping of a body lumen 16. Alternatively, the EAP RO Markers 10 may separate from a catheter system 18 due to the Marker 10 having an increased diameter relative to the catheter 18. Thereafter, the catheter 18 may be inserted further within the body lumen or withdrawn without further contact with a Marker 10. The EAP RO Markers 10 may be detached/separated from the catheter system 18 by any conventional technique including the use of a sacrificial detachable or severable joint. The sacrificial detachable severable joint may be severed using any number of mechanisms including, but not limited to, electrolytic corrosion, mechanical actuation, hydraulic pressure, thermal processes, and/or electromagnetic energy. Other methods of detachment not described herein, but known in the art, may also be employed in detaching the device of the present invention. As noted above, severable junctions are described, for example, in U.S. Pat. Nos. 5,122,136; 5,354,295; 5,540,680; 5,855,578; 5,895,385; 5,925,037; 5,944,714; 5,947,963; 5,977,612; 6,010,498; 6,066,133; and 6,083,220; each of which is incorporated by reference herein in its entirety.

In some embodiments, following separation from the catheter system 18, the EAP RO Marker 10, as expanded into the delivery state, will preferably frictionally engage the interior of the body lumen 16 proximate to the bifurcation 14.

In some embodiments, once the EAP RO Markers 10 have been deployed in the delivery state, it is anticipated that the expanded delivery state will be maintained, so long as the Marker 10 remains within the body lumen 16. It is believed that bodily fluids exposed to the EAP RO Markers 10 will provide a sufficient source of anions to deter contraction of the Marker 10 into a pre-delivery state.

In some embodiments, the procedure for the use of a retractable EAP RO Markers 10 is similar to the procedure as identified above. During a medical procedure, where a retractable EAP RO Marker 10 is used, another type of implantable medical device 36, such as a stent, is separated for deployment within a body lumen 16. The exposure of anions to the EAP RO Marker 10 assist a medical provider in viewing the location of the implantable medical device 36 as adjacent to a bifurcation 14 and/or other stenosis, such as an aneurism. Improved accuracy in the placement of an implantable medical device 36 may therefore be achieved.

In an alternative embodiment, one or more EAP RO Markers 10 may be temporarily separated from a catheter system 18 during a medical procedure to map bifurcation areas 14 to assist a medical provider in repeat medical procedures. In this application, the mapping of a body lumen 16 identifies any number of bifurcation pathways. Any desired number of EAP RO Markers 10 may therefore be temporarily separated from catheter system 18 to map a body lumen 16 during placement of an implantable medical device 36.

In an alternative embodiment, any desired number of EAP RO Markers 10 may be sequentially separated from a catheter system 18. Each of the EAP RO Markers 10 is preferably initially transported in the pre-delivery state. A series of sequential EAP RO Markers 10 may then be individually exposed to anions for separation from the catheter system 18 at a bifurcation or branch passageway 14. One or more independent electrical pathways may be necessary to accomplish independent expansion and/or separation from a catheter system 18.

Once a medical procedure as been completed a catheter system 18 may be withdrawn. At each bifurcation or branch, previously marked with an EAP RO Marker 10, electricity may be provided to generate cations to contract an EAP RO Markers 10 into a pre-delivery state on the catheter system 18. The contraction of a previously expanded EAP RO Markers 10 may occur about the exterior circumference of the catheter system 18. Any number of temporarily placed EAP RO Markers 10 may then be picked up for withdraw from a body lumen 16 upon a completion of the medical procedure.

A medical provider may utilize any combination of leave behind or retractable EAP RO Markers 10 during a medical procedure as desired.

In some embodiments, the EAP RO Markers 10 may also be at least partially coated with a drug or other substance. Drugs and coatings thereof are well known. The application of such a coating to an EAP RO Markers 10 allows the marker 10 to deliver the drug directly to a desired location within the vessel. However, in many applications it may be of importance to ensure that the concentration, amount, or exposure of the drug along a given length of the marker 10 is substantially consistent. In the various embodiments drug coating may be comprised of any or all of a variety of drugs, genetic material, non-genetic therapeutic agents, cells, and/or cellular material, polymer coatings, viruses, retro-viruses, and/or other substances. In some embodiments, the coating is at least partially radiopaque.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS) polyethylene oxide, silicone rubber and/or any other suitable substrate.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A marker device, said marker device is adapted for implantation in a subject and is expandable and/or contractible, said marker device comprising radiopaque material, at least one pre-delivery state, at least one delivery state, and at least one active region, the at least one active region comprising electroactive polymer material.

2. The marker device of claim 1 wherein the electroactive polymer material is an electric electroactive polymer or an ionic electroactive polymer.

3. The marker device of claim 2 wherein said electroactive polymer material is an ionic electroactive polymer selected from the group consisting of conductive polymers, ionic polymer gels, ionomeric polymer-metal composites, carbon nanotubes and mixtures thereof.

4. The marker device of claim 3 wherein said ionic electroactive polymer is a conductive polymer selected from the group consisting of polypyrroles, polyanilines, polythiophenes, polyethylenedioxythiophenes, poly(p-phenylene vinylene)s, polysulfones, polyacetylenes and mixtures thereof.

5. The marker device of claim 1 wherein said radiopaque material is embedded within said marker device.

6. The marker device of claim 1, said marker device comprising a framework of said electroactive polymer material and said radiopaque material, said radiopaque material selected from the group consisting of barium, bismuth, titanium, platinum, iridium, rhenium, gold, tantalum, tungsten, palladium, rhodium, silver, niobium, molybdenum, latnium, and combinations thereof.

7. The marker device of claim 6, said radiopaque material comprising radiopaque polymers.

8. The marker device of claim 1 further comprising a plurality of said active regions.

9. The marker device according to claim 1 wherein said radiopaque material is integral to said marker device.

10. A method of pre-mapping a region of a body lumen comprising;
 a) providing a marker device comprising electroactive polymer material and radiopaque material;
 b) engaging said marker device to catheter;
 c) advancing said catheter to a location in a body lumen;
 d) exposing said marker device to electricity;
 e) withdrawing said catheter whereby said marker device is left behind; and
 f) detecting said marker using at least one imaging modality.

11. The method according to claim 10 said marker further comprising at least one pre-delivery state and at least one delivery state.

12. The method according to claim 11 said at least one pre-delivery state comprising an outer diameter, said at least one delivery state comprising a second outer diameter.

13. The method according to claim 12 wherein said at least one pre-delivery state outer diameter is less than said at least one delivery state second outer diameter.

14. The method according to claim 13 said exposure to electricity comprising exposure to anions.

15. The method according to claim 12 wherein said at least one pre-delivery state outer diameter is greater than said at least one delivery state second outer diameter.

16. The method according to claim 14 wherein said exposure to anions transitions said marker from said at least one pre-delivery state to said at least one delivery state.

17. The method according to claim 16 wherein said delivery second outer diameter frictionally engages said body lumen.

18. A method according to claim 16 said method further comprising providing a plurality of marker devices.

19. The method according to claim 16 said method further comprising positioning at least one of said marker devices proximate to a bifurcation of vessels.

20. The method according to claim 19 wherein at least one of said marker devices is positioned in a first vessel, adjacent to an ostium of a second vessel.

21. The method according to claim 19 wherein said marker device is positioned in a second vessel, the second vessel branching from the first vessel.

* * * * *